United States Patent
Matsumoto et al.

(10) Patent No.: US 9,962,680 B2
(45) Date of Patent: May 8, 2018

(54) POLYACRYLIC ACID (SALT)-BASED WATER ABSORBENT RESIN, AND METHOD FOR PRODUCTION THEREOF

(75) Inventors: Satoshi Matsumoto, Himeji (JP); Kunihiko Ishizaki, Himeji (JP); Kanako Tsuru, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 389 days.

(21) Appl. No.: 13/994,871

(22) PCT Filed: Dec. 16, 2011

(86) PCT No.: PCT/JP2011/079219
§ 371 (c)(1),
(2), (4) Date: Jun. 17, 2013

(87) PCT Pub. No.: WO2012/081702
PCT Pub. Date: Jun. 21, 2012

(65) Prior Publication Data
US 2013/0264517 A1    Oct. 10, 2013

(30) Foreign Application Priority Data
Dec. 17, 2010 (JP) .................. 2010-281382

(51) Int. Cl.
B01J 20/26     (2006.01)
B01J 20/28     (2006.01)
B01J 20/30     (2006.01)
A61L 15/60     (2006.01)
C08F 220/06    (2006.01)
C08F 222/10    (2006.01)

(52) U.S. Cl.
CPC ............ B01J 20/261 (2013.01); A61L 15/60 (2013.01); B01J 20/28014 (2013.01); B01J 20/3092 (2013.01); C08F 220/06 (2013.01); C08F 222/1006 (2013.01)

(58) Field of Classification Search
CPC .................... B01J 20/261; B01J 20/3092; B01J 20/28014; A61L 15/60; C08F 220/06; C08F 222/1006
See application file for complete search history.

(56) References Cited

U.S. PATENT DOCUMENTS

| | | |
|---|---|---|
| 5,115,011 A | 5/1992 | Harada et al. |
| 5,210,298 A | 5/1993 | Shimomura et al. |
| 5,229,488 A | 7/1993 | Nagasuna et al. |
| 6,388,000 B1 | 5/2002 | Irie et al. |
| 6,552,141 B1 | 4/2003 | Chmelir et al. |
| 6,914,099 B2 | 7/2005 | Kim |
| 7,030,199 B1 | 4/2006 | Chmelir et al. |
| 8,648,161 B2 * | 2/2014 | Fujino et al. ............. 526/317.1 |
| 2005/0154146 A1 | 5/2005 | Irie et al. |
| 2008/0194863 A1 | 8/2008 | Weismantel et al. |
| 2008/0242816 A1 | 10/2008 | Weismantel et al. |
| 2009/0221746 A1 | 9/2009 | de Marco et al. |
| 2009/0321682 A1 | 12/2009 | Kajikawa et al. |
| 2011/0003926 A1 | 1/2011 | Nogi et al. |
| 2011/0034603 A1 | 2/2011 | Fujino et al. |
| 2011/0306732 A1 | 12/2011 | Fujino et al. |
| 2012/0010372 A1 | 1/2012 | Fujino et al. |
| 2012/0059138 A1 | 3/2012 | de Marco et al. |

FOREIGN PATENT DOCUMENTS

| | | |
|---|---|---|
| EP | 0505163 | 3/1992 |
| EP | 2112172 A | 10/2009 |
| JP | 6-56931 | 3/1994 |
| JP | 2005-008705 | 1/2005 |
| JP | 2005-530906 | 10/2005 |
| JP | 2009-545635 | 12/2009 |
| WO | 1994/015971 | 7/1994 |
| WO | 2007/028747 | 3/2007 |
| WO | 2010/090324 | 8/2010 |
| WO | WO2010090324 | * 8/2010 |

OTHER PUBLICATIONS

Buchholz et al., "Modern Superabsorbent Polymer Technology," pp. 39-44 (1998).

* cited by examiner

*Primary Examiner* — Peter F Godenschwager
*Assistant Examiner* — Andrew J Oyer
(74) *Attorney, Agent, or Firm* — Cesari and McKenna, LLP

(57) ABSTRACT

Provided is a method for producing a polyacrylic acid (salt)-based water absorbent resin, which is a convenient production method for a water absorbent resin for an absorbent suitable for practical use, the water absorbent resin having a reduced amount of residual monomers. Disclosed is a method for producing a polyacrylic acid (salt)-based water absorbent resin, the method comprising a polymerization step of polymerizing an aqueous monomer solution containing acrylic acid (salt) as a main component; a drying step of drying a water-containing gel-like crosslinked polymer obtained in the polymerization step; a surface crosslinking step of surface crosslinking the water absorbent resin under drying or the water absorbent resin which has been dried; and a packaging step of packaging the surface crosslinked water absorbent resin, wherein an iron content in the aqueous monomer solution in the polymerization step is 2 ppm (relative to the monomer(s)) or less, a moisture content of the water absorbent resin in the packaging step is 1% by weight or more, and the method further comprises, after the packaging step, a storage step of storing the packaged water absorbent resin for 3 days or longer.

20 Claims, No Drawings

POLYACRYLIC ACID (SALT)-BASED WATER ABSORBENT RESIN, AND METHOD FOR PRODUCTION THEREOF

CROSS REFERENCE TO RELATED APPLICATIONS

This application is a National Stage of International Application No. PCT/JP2011/079219 filed on Dec. 16, 2011, which claims priority to Japanese Application No. 2010-281382 filed Dec. 17, 2010, the contents of which are hereby incorporated by reference in their entirety.

TECHNICAL FIELD

The present invention relates to a polyacrylic acid (salt)-based water absorbent resin and a method for production thereof. More particularly, the present invention relates to a water absorbent resin for absorbents that are used in paper diapers, sanitary napkins and the like, and a method for production thereof, and the invention also relates to a polyacrylic acid (salt)-based water absorbent resin which has excellent yellowing resistance, produces less foul odor, and exhibits excellent absorption capacity, and a method for production thereof.

BACKGROUND ART

In recent years, a water absorbent resin having high water absorbency has been developed and often used primarily in disposable applications as absorbent articles such as paper diapers and sanitary napkins, as well as water retention agents for agricultural and horticultural use, industrial water stopping material, and the like. As for such water absorbent resins, many hydrophilic polymers and monomers as raw materials thereof have been proposed, and among them, polyacrylic acid (salt)-based water absorbent resins that use acrylic acid and/or salt thereof as a monomer have been industrially most frequently used, due to their high water absorption performance. Such a polyacrylic acid (salt)-based water absorbent resin is obtained as a polyacrylate by neutralizing acrylic acid and then polymerizing the product, or by polymerizing acrylic acid and then neutralizing polyacrylic acid thus obtained. Such neutralization and polymerization processes are disclosed in Patent Documents 1 to 4 or Non-Patent Document 1.

Also, since the primary use of the water absorbent resins lies in hygienic materials such as paper diapers and sanitary napkins, particular caution is taken for safety. Especially, since a proportion of water absorbent resins in diapers is increasing recently, water absorbent resins containing a reduced amount of highly reactive components, for example, residual monomers in the water absorbent resins are preferred. On the other hand, because residual monomers such as acrylic acid (salts) have an acid odor, also from the viewpoint of odor of the water absorbent resin, water absorbent resins having reduced amounts of residual monomers are preferred. Regarding the method for producing such a water absorbent resin, various technologies have been proposed, and for example, in order to reduce an amount of residual monomers that are generated in heat-treating a polymer, a method of performing polymerization using an acrylic acid containing a reduced amount of acrylic acid dimer (Patent Document 5), a method of performing polymerization using an aqueous monomer solution with a reduced amount of β-hydroxypropionic acid (Patent document 6), and the like have been known. Furthermore, as methods for reducing an amount of residual monomers by using an additive, a method of adding a nitrogen compound (Patent Documents 7 and 8), particularly a method of performing neutralization with ammonia (Patent Document 6), a method of adding a persulfuric acid salt to a polymer and heating the polymer (Patent Document 9), a method of adding a reducing agent to a water-containing gel and heating the water-containing gel (Patent Document 10), a method of adding a reducing agent, and a surfactant and/or water-insoluble fine particles to a water absorbent resin and heating the mixture (Patent Document 11), a method of adding any one of an inorganic reducing agent, an initiator, an oxidizing agent and a reducing agent to a fine powder and granulating the mixture to form a gel, and heating the gel (Patent Document 12), a method of adding a photoinitiator and then exposing the mixture to sunlight (Patent Document 13), and the like have been known. Also, a method of promoting reduction of an amount of residual monomers in a drying step by using a particular drying method has been known (Patent Document 14).

However, although trace components in acrylic acid or an aqueous monomer solution are controlled, there have been limitations on an amount of residual monomers that can be reduced only by suppressing the residual monomers that newly increase when the polymer is heat-treated. Furthermore, in the case where an additive is used, even if the residual monomers could be reduced, it is disadvantageous in view of cost, and also, there may be a problem with the safety of the additive itself, or there may be occasions where coloration occurs particularly when the polymer is heated, or a foul odor different from that of the residual monomers may be generated. Therefore, none of the products was found to be preferable as a water absorbent resin. Furthermore, due to use of large amounts of additives, there have been problems such as an increase in cost, as well as coloration and generation of foul odor of water absorbent resin, and a decrease in the water absorption performance, which are caused by additives.

CITATION LIST

Patent Document

Patent Document 1: U.S. Pat. No. 5,210,298
Patent Document 2: US-A-2008/242816
Patent Document 3: WO 2007/28747 A
Patent Document 4: US-A-2008/194863
Patent Document 5: WO 1994/015971 A
Patent Document 6: U.S. Pat. No. 6,388,000
Patent Document 7: U.S. Pat. No. 6,552,141
Patent Document 8: U.S. Pat. No. 7,030,199
Patent Document 9: U.S. Pat. No. 6,914,099
Patent Document 10: EP-0505163
Patent Document 11: U.S. Pat. No. 5,229,488
Patent Document 12: U.S. Pat. No. 5,115,011
Patent Document 13: JP-A-2005-008705
Patent Document 14: U.S. Pat. No. 620,796

Non-Patent Document

Non-Patent Document 1: Modern Superabsorbent Polymer Technology, p. 39-44 and the like

SUMMARY OF INVENTION

Problem to be Solved by the Invention

A problem to be solved of the present invention is to provide a water absorbent resin for an absorbent which has a reduced amount of residual monomers and is suitable for practical use, and a convenient method for production thereof, in relation to a polyacrylic acid (salt)-based water absorbent resin and a method for production thereof.

Means to Solve the Problem

In view of the problems described above, the present inventors have conducted an investigation on a method for reducing an amount of residual monomers, to find conditions under which the amount of residual monomers can be reduced without a heat treatment or an additive. More particularly, the present inventors have paid attention for the first time to a storage period from packaging to shipping of a water absorbent resin, and found that by adjusting the storage period to a predetermined range, an amount of residual monomers can be reduced without changing various properties of the water absorbent resin. Thus, the inventors have completed the present invention.

Specifically, in order to solve the above problems, a method for producing a polyacrylic acid (salt)-based water absorbent resin according to the present invention comprises a polymerization step of polymerizing an aqueous monomer solution containing acrylic acid (salt) as a main component, a drying step of drying a water-containing gel-like crosslinked polymer obtained in the polymerization step, a surface crosslinking step of surface crosslinking the water absorbent resin under drying or the water absorbent resin which has been dried, and a packaging step of packaging the surface crosslinked water absorbent resin, wherein an iron content in the aqueous monomer solution in the polymerization step is 2 ppm (relative to the monomer(s)) or less, a moisture content of the water absorbent resin in the packaging step is 1% by weight or more, and the method further comprises, after the packaging step, a storage step of storing the packaged water absorbent resin for 3 days or longer.

In order to solve the above problems, a polyacrylic acid (salt)-based water absorbent resin according to the present invention has an iron content of 2 ppm or less, a moisture content of 1% by weight or more, and a p-methoxyphenol content of 5 ppm to 60 ppm, and comprises at least one or more aggregation preventing agents selected from the group consisting of polyvalent metal salts, water-insoluble fine particles, and surfactants, and/or at least one or more coloration preventing agents selected from the group consisting of α-hydroxycarboxylic acid compounds, inorganic reducing agents, and chelating agents.

Effects of Invention

According to the present invention, a water absorbent resin for an absorbent which has a reduced amount of residual monomers and is suitable for practical use, and a method for production thereof can be provided.

EMBODIMENT(S) FOR CARRYING OUT THE INVENTION

Hereinafter, a method for producing a polyacrylic acid (salt)-based water absorbent resin related to the present invention will be described in detail. However, the scope of the present invention is not intended to be limited to these descriptions, and embodiments other than the following embodiments can also be appropriately modified and carried out to an extent that the scope of the present invention is not impaired. Specifically, the present invention is not intended to be limited to the various exemplary embodiments described below, and can be modified into various embodiments within the scope defined by the claims. Exemplary embodiments which can be obtained by appropriately combining the technical means that are respectively disclosed in different exemplary embodiments, are also included in the technical scope of the present invention.

[1] Definitions of Terms (1-1) "Water Absorbent Resin"

The term "water absorbent resin", as used herein, is referred to a water-swellable, water-insoluble polymer gelling agent, which has the following properties. That is, the "water absorbent resin" refers to a polymer gelling agent having CRC (absorption capacity without load) as defined in ERT441.2-02 (2002) of 5 [g/g] or higher in terms of "water-swellable" property, and Ext (Extractables) as defined in ERT470.2-02 (2002) of 0% to 50% by weight in terms of "water-insoluble" property.

The water absorbent resin can be appropriately designed in accordance with its application, and there are no particular limitations. However, the water absorbent resin is preferably a hydrophilic crosslinked polymer obtained by crosslinking polymerizing an unsaturated monomer having a carboxyl group. Furthermore, the water absorbent resin is not limited to the case in which the water absorbent resin consists of a polymer in its entire amount (100% by weight), and the water absorbent resin may contain an additive and the like to an extent that the performance described above is maintained. Furthermore, the water absorbent resin of the present invention is not intended to be limited to a final product, and may refer to an intermediate obtainable in the production process for a water absorbent resin (for example, a water absorbent resin obtainable after drying or before surface crosslinking). Thus, these are all collectively referred to as a water absorbent resin.

(1-2) "Polyacrylic Acid (Salt)"

The term "polyacrylic acid (salt)", as used herein, is referred to as a polymer containing an arbitrary graft component, and having as a main component acrylic acid and/or a salt thereof (hereinafter, referred to as acrylic acid (salt)) as a repeating unit.

That is, the polyacrylic acid (salt) refers to a polymer having a content (amount of use) of acrylic acid (salt) relative to the total amount of the monomers used in polymerization (excluding an internal crosslinking agent) of usually 50% to 100% by mole, preferably 70% to 100% by mole, more preferably 90% to 100% by mole, and particularly preferably substantially 100% by mole. Furthermore, the polyacrylic acid as a polymer essentially includes a water-soluble salt, and the water-soluble salt is preferably a monovalent salt, and more preferably an alkali metal salt or an ammonium salt.

(1-3) "EDANA" and "ERT"

The term "EDANA" is an abbreviation for the European Disposables and Nonwovens Associations, and the term "ERT" is an abbreviation of measurement method for a water-absorbent resin of an European standard (nearly a world standard) (EDANA Recommended Test Method). In the present description, unless otherwise specified, physical properties of a water-absorbent resin are measured based on the ERT original (known document: revised in 2002).

(a) "CRC" (ERT441.2-02)

The term "CRC" is an abbreviation for Centrifuge Retention Capacity, and means absorption capacity without load (hereinafter, also be referred to as "absorption capacity"). Specifically, the CRC is absorption capacity (unit; [g/g])

obtained after 0.200 g of a water absorbent resin in a non-woven fabric is allowed to freely swell for 30 minutes in a 0.9 wt % aqueous solution of sodium chloride, and then water is drained therefrom in a centrifuge (250G).

(b) "AAP" (ERT442.2-02)

The term "AAP" is an abbreviation for Absorption Against Pressure, and means absorption capacity under load. Specifically, the AAP is absorption capacity (unit; [g/g]) obtained after adding 0.900 g of a water absorbent resin to a 0.9 wt % aqueous solution of sodium chloride, and causing the water absorbent resin to swell for one hour under a load of 2.06 kPa (0.3 psi). Meanwhile, the measurement may also be made by changing the load conditions to 4.83 kPa (0.7 psi).

(c) "Ext" (ERT470.2-02)

The term "Ext" is an abbreviation for Extractables, and means a water-soluble content. Specifically, the Ext is an amount of dissolved polymer (unit; wt %) obtained after adding 1.000 g of a water absorbent resin to 200 ml of a 0.9 wt % aqueous solution of sodium chloride, and stirring the mixture for 16 hours. The measurement of the amount of dissolved polymer is carried out by pH titration.

(d) "RM" (ERT410.2-02)

The term "RM" is an abbreviation for Residual Monomers, and means an amount of monomers remaining in a water absorbent resin (hereinafter, also referred to as "residual monomers"). Specifically, the RM refers to an amount of eluted monomers (unit; ppm by weight) obtained after adding 1.0 g of a water absorbent resin to 200 ml of a 0.9 wt % aqueous solution of sodium chloride, and stirring the mixture at a speed of 500 rpm for one hour. Meanwhile, the measurement of the amount of residual monomers is carried out by using HPLC (high performance liquid chromatography).

(e) Other Physical Properties Defined by EDANA

"pH" (ERT400.2-02): means pH of a water absorbent resin.

"PSD" (420.2-02): means a particle size distribution that is measured by sieve classification of a water absorbent resin. Meanwhile, PSD is an abbreviation for Particle Size Distribution.

"Moisture Content" (ERT430.2-02): means a moisture content of a water absorbent resin. The moisture content in the present invention is measured by the method described in Examples.

"Flow Rate" (ERT450.2-02): means a speed of flow-down speed of a water absorbent resin.

"Density" (ERT460.2-02): means a bulk specific gravity of a water absorbent resin.

(1-4) Liquid Permeability

The term "liquid permeability", as used herein, refers to fluid flow among swollen gel particles under load or without load. As a typical evaluation method thereof, there is an evaluation method of SFC (Saline Flow Conductivity) and GBP (Gel Bed Permeability).

The term "SFC" (Saline Flow Conductivity)" means liquid permeability of a 0.69 wt % aqueous solution of sodium chloride for a water absorbent resin under load of 2.07 kPa. It is measured in accordance with SFC test described in U.S. Pat. No. 5,669,894. Furthermore, the term "GBP" means liquid permeability of a 0.69 wt % aqueous solution of sodium chloride for a water absorbent resin under load or in free expansion. It is measured in accordance with GBP test described in WO 2005/016393.

(1-5) "Initial Color Tone" and "Color Tone Over Time"

The term "initial color tone", as used herein, means color tone of a water absorbent resin immediately after production or immediately after user shipment, and usually, the initial color tone is regarded as color tone before factory shipment. Furthermore, the term "color tone over time" refers to color tone of a water absorbent resin after storage for a long period in an unused state, or after the course of distribution. The color tone is measured according to the method disclosed in WO 2009/005114 (Lab values, YI value, WB value, and the like).

(1-6) Others

In the present description, "X to Y" showing a range indicates to be equal to or higher than X and equal to or lower than Y. Also, "t (ton)" as a unit of weight means "Metric Ton". Unless otherwise specified, "ppm" should mean "ppm by weight" or "ppm by mass". In the present description, "mass", "% by mass" and "parts by mass" are used synonymously to "weight", "% by weight" and "parts by weight", respectively. Furthermore, the term " . . . acid (salt)" means " . . . acid and/or salt thereof", and "(meth) acrylic" means "acrylic and/or methacrylic".

[2] Method for Producing Polyacrylic Acid (Salt)-Based Water Absorbent Resin

The method for producing a polyacrylic acid (salt)-based water absorbent resin according to the present invention is a method for producing a polyacrylic acid (salt)-based water absorbent resin, which comprises a polymerization step of polymerizing an aqueous monomer solution containing acrylic acid (salt) as a main component, a drying step of drying a water-containing gel-like crosslinked polymer obtained in the polymerization step, a surface crosslinking step of surface crosslinking the water absorbent resin under drying or the water absorbent resin which has been dried, and a packaging step of packaging the surface crosslinked water absorbent resin, wherein an iron content in the aqueous monomer solution in the polymerization step is 2 ppm (relative to the monomer(s)) or less, a moisture content of the water absorbent resin in the packaging step is 1% by weight or more, and the method further comprises, after the packaging step, a storage step of storing the packaged water absorbent resin for 3 days or longer.

Here, in order to solve the problems, it is necessary to control an iron content in the aqueous monomer solution to 2 ppm (with respect to the monomer(s)) or less and a moisture content of the water absorbent resin to 1% by weight or more, and after packaging, to store the water absorbent resin in a packaged state for a predetermined time or longer. If the moisture content is less than 1% by weight, an effect of reducing an amount of residual monomers cannot be obtained, and if the iron content is larger than 2 ppm, an increase in residual monomers and coloration and deterioration of the water absorbent resin are observed, which is not preferable. Furthermore, when the water absorbent resin is stored for a predetermined time after being packaged, an amount of residual monomers can be reduced, and physical properties can be stabilized. Meanwhile, the moisture content at the time of packaging the water absorbent resin is preferably 3% to 20% by weight.

Also, in order to solve the problems, it is preferable to adjust a p-methoxyphenol content in the aqueous monomer solution in the polymerization to 5 ppm to 160 ppm (aqueous monomer solution; with respect to the monomers), or a p-methoxyphenol content in the water absorbent resin in the packaging to 5 ppm to 60 ppm (water absorbent resin). By preventing the p-methoxyphenol content from exceeding the upper limit, an increase in residual monomers or deterioration of the color tone can be prevented. On the other hand, when the p-methoxyphenol content is prevented from falling below the lower limit, unexpected polymerization (monomers) or deterioration of weather resistance (water absorbent resin) can be prevented.

Furthermore, in order to solve the problems, it is preferable to adjust a total content of acetic acid and propionic acid in the aqueous monomer solution in the polymerization to 1500 ppm (with respect to the monomers) or less. When the total content of acetic acid and propionic acid is adjusted to be equal to or less than the upper limit, even if the water absorbent resin is stored in a packaged state for a predetermined time, the generation of an acid odor originating from acetic acid and propionic acid in a packaging material (bag, container or the like) can be suppressed.

Furthermore, in order to solve the problems, in the present invention in which a water absorbent resin having a moisture content of 1% by weight or more, and preferably 3% to 20% by weight, is stored for a predetermined time, it is preferable to further comprise, in order to prevent aggregation of the water absorbent resin during the packaging step or the storage step or thereafter, an addition step of adding at least one or more aggregation preventing agents selected from the group consisting of polyvalent metal salts, water-insoluble fine particles, and surfactants to the water absorbent resin before the packaging step.

Furthermore, in order to solve the problems, in the present invention in which a water absorbent resin having a moisture content of 1% by weight or more, and preferably 3% to 20% by weight, is stored for a predetermined time, it is preferable to further comprise, in order to prevent coloration of the water absorbent resin during the packaging step or the storage step or thereafter, an addition step of adding at least one or more coloration preventing agents selected from the group consisting of α-hydroxycarboxylic acid compounds, inorganic reducing agents, and chelating agents to the water absorbent resin before the packaging step.

Furthermore, in order to solve the problems, it is preferable that
a packaging container used in the packaging step is any one of a plastic container and a container having a plastic inner bag, both of which are capable of transporting the water absorbent resin in a unit amount of 15 kg to 10 t, more preferably in a unit amount of 20 kg to 10 t. Use of such a packaging container is advantageous from the viewpoints of moisture proofing and prevention of dew condensation. Furthermore, it is preferable that
a travel distance for the water absorbent resin in the storage step is 10 km or less
a travel distance travelled by the water absorbent resin in a packaged state after the packaging of the water absorbent resin to the storage place or the like during the storage step, be 10 km or less. When the travel distance is adjusted to be equal to or less than the upper limit, the generation of fine dust caused by damage occurring during transportation, or the occurrence of segregation in the container due to the difference in the particle size can be suppressed.

Furthermore, in order to solve the problems, it is preferable to perform surface crosslinking by essentially using a crosslinking agent other than an epoxy crosslinking agent in the surface crosslinking step; it is more preferable to perform surface crosslinking by using a dehydration reactive surface crosslinking agent; and it is particularly preferable to perform surface crosslinking by using a dehydration reactive surface crosslinking agent and an ion-reactive crosslinking agent in combination. By using such a crosslinking agent, a dehydration reaction can be controlled by heating conditions that will be described below, and a water absorbent resin exhibiting excellent absorption under load can be easily obtained. Furthermore, since a crosslinked layer formed by this process and a residual dehydration reactive crosslinking agent hardly undergo any change or reaction during the storage step for the water absorbent resin, it is preferable also from the stability of physical properties.

Furthermore, in order to solve the problems, in the present invention in which a water absorbent resin having a moisture content of 1% by weight or more, and preferably 3% to 20% by weight, is stored for a long time, it is preferable to carry out a storage step in a storage place equipped with an apparatus for controlling at least one or more of air temperature and humidity, and it is more preferable that the air temperature in the storage place be 5° C. to 60° C., and the relative humidity be 10% to 700. When the storage step is carried out in such an environment, formation of aggregations or coloration over time during the storage step can be reduced.

It is also preferable to measure physical properties of the water absorbent resin at least one or more times during the storage step. When physical properties are measured during the storage step, measurement values with less fluctuation can be obtained. Meanwhile, the physical properties measurement may include measurement of, for example, CRC, AAP, moisture content, residual monomers and the like, but not limited thereto. Sampling in the measurement of physical properties is preferably carried out such that in order not to significantly destroy an environment under sealing, breaking of sealing is temporary, preferably within 3 hours, and more preferably within 1 hour, with the breaking of sealing being kept minimal. Such physical properties measurement is included in the storage step.

For the sampling method in the physical properties measurement, it would be desirable if a certain amount (for example, several ten grams to several hundred grams) of water absorbent resin could be sampled from a surface layer (upper part), a lower layer (lower part) or an interior of a water absorbent resin powder in a storage container, and there are no particular limitations. However, in the case of performing sampling from plural containers of the same specifications, it is preferable to perform sampling from the same position (height) from the viewpoint of reproducibility of data. Also, examples of the instrument for sampling may include a scoop, a ladle, a cup, a sampling spear and the like, and a sampling spear which is capable of sampling from an interior of a powder layer of a water absorbent resin is preferred.

Furthermore, in order to solve the problems, it is preferable that ammonium acrylate be included in an aqueous monomer solution containing acrylic acid (salt) as a main component in the polymerization, in an amount of equal to or more than 1% by mole and less than 90% by mole relative to the total amount of monomers, in order to reduce an amount of residual monomers. Also, in order to reduce the amount of residual monomers more effectively, it is preferable to adjust an amount of residual monomers in a water absorbent resin in the packaging to 300 ppm or less, and to store the water absorbent resin until the amount of residual monomers is reduced by 10 ppm or more in the storage step after packaging.

Hereinafter, each constitution related to the present production method will be described in order.

(2-1) Acrylic Acid (Salt)

The acrylic acid (salt) used in the present invention contains trace components described below, or have trace components added thereto as necessary.

In the present invention, acrylic acid is produced by a known method (for example, a production process for acrylic acid including catalytic oxidation of propane or propylene in one stage or two stages, collection, and one time or several times of distillation or crystallization). From the viewpoint of reducing residual monomers, it is preferable that a production process for acrylic acid be connected to a process for producing a water absorbent resin, and it is particularly preferable that the two production processes be connected by a pipeline(s).

Furthermore, while the pipelines may connect each the production processes for acrylic acid with the production process (polymerization step) for a water absorbent resin, it is particularly preferable that only a final purification step for acrylic acid (in the case of performing multi-stage purification, a last purification step (particularly, a final distillation or crystallization)) be connected to the process for producing a water absorbent resin. By continuously supplying acrylic acid that is obtained immediately after purification to a polymerization step for water absorbent resin through a pipeline(s), residual monomers can be further reduced, and the water absorbent resin is further stabilized in terms of residual monomers and other physical properties. Moreover, in addition to acrylic acid, vapor produced in an acrylic acid production process can also be easily supplied to a process for producing a water absorbent resin through a pipeline(s), and can be used for energy in the drying step or the like for a water absorbent resin. Therefore, residual monomers are further reduced.

Furthermore, during the production process for acrylic acid, acrylic acid is obtained not as an aqueous solution (for example, a 80 wt % aqueous acrylic acid solution), but as acrylic acid with a purity of 99% to 100% by weight and containing a small amount of water.

The pipelines are kept warm or heated to preferably 18° C. to 40° C., and more preferably 20° C. to 30° C. Also, acrylic acid may be stored as necessary after purification, and a period therefor is preferably 30 days or less after purification, more preferably 10 days or less after purification, still more preferably 5 days or less after purification, particularly preferably 3 days or less after purification, and most preferably 1 day or less after purification. When acrylic acid is supplied to the polymerization step for a water absorbent resin and consumed therein after the storage period has passed, residual monomers can be further reduced.

Although the present invention attempts to reduce residual monomers by providing a storage step of a water absorbent resin for a predetermined period or longer as will be described below, for acrylic acid as the raw material, it is more preferable that the storage period is as short as possible. Preferably, the storage period is adjusted to the period described above, and particularly preferably, the raw material acrylic acid is continuously supplied through a pipeline(s).

(a) Iron Component

In the present invention, in order to solve the problems, a iron content in an aqueous monomer solution is controlled to 2 ppm or less (relative to a solid content of monomers), and preferably 0.01 ppm to 1 ppm. The iron components are believed to originate from acrylic acid, a basic substance used for neutralization of acrylic acid, a component eluted from a storage tank, piping and the like after the preparation of an aqueous monomer solution, and the like. Particularly, when the iron component originate from the basic substance, the content thereof is preferably 0.01 ppm to 10 ppm, more preferably 0.1 ppm to 5 ppm, and still more preferably 0.3 ppm to 3 ppm, relative to the basic substance.

If the iron content is less than the range described above, the aqueous monomer solution would become unstable, and unexpected polymerization would occur. Furthermore, if it exceeds the range described above, polymerization would be delayed, and an increase in residual monomers or coloration of a water absorbent resin would occur, which is not preferable. Particularly, if the iron content is larger than 2 ppm in the storage step for a predetermined time in the present invention, a problem of coloration of a water absorbent resin would occur, which is not preferable.

Meanwhile, regarding the iron components in the present invention, there are no particular limitations on a counterion of Fe, and Fe ion may be included. However, from the viewpoint of the effect, trivalent iron compounds are preferred, and particularly, iron(III) hydroxide ($Fe(OH)_3$) or iron(III) oxide ($Fe_2O_3 \cdot nH_2O$) is preferred.

(b) Phenolic Compound

In the present invention, in order to solve the problems, it is preferable that an aqueous monomer solution or a water absorbent resin contain a predetermined amount of a phenolic compound as a polymerization inhibitor. Examples of the phenolic compound include alkylphenols, alkoxyphenols and the like, and suitable examples of alkyl groups that are contained in these compounds include a t-butyl group, a methyl group, an ethyl group and the like. Among these, a particularly preferred polymerization inhibitor is p-methoxyphenol.

An used amount (content) of the phenolic compound in the aqueous monomer solution is preferably 5 ppm to 160 ppm, more preferably 5 ppm to 130 ppm, still more preferably 5 ppm to 100 ppm, particularly preferably 5 ppm to 60 ppm, and most preferably 5 ppm to 30 ppm, relative to the monomer components that include acrylic acid (salt) as a main component. Furthermore, an used amount (content) of the phenolic compound in the water absorbent resin is preferably 5 ppm to 60 ppm, and more preferably 5 ppm to 30 ppm, relative to the water absorbent resin. By controlling the used amount (content) of the polymerization inhibitor in the aqueous monomer solution to a value equal to or less than the upper limit, delay of the reaction in the polymerization step can be prevented. Also, by adjusting the used amount (content) of the polymerization inhibitor in the aqueous monomer solution or water absorbent resin within the range described above, coloration of the resultant water absorbent resin can be suppressed. Furthermore, prevention of deterioration of the water absorbent resin in the storage step that will be described below can be attained. If the used amount (content) of the polymerization inhibitor is less than 5 ppm, there would be a risk that unexpected polymerization may occur in the aqueous monomer solution.

Here, the phenolic compound in the monomers tends to be consumed by operations such as polymerization and drying. Therefore, the amount of the phenolic compound in the polymerization may be reduced to about ⅕ to 1/20 by a method that will be described below.

(c) Saturated Carboxylic Acid

The acrylic acid (salt) used in the present invention can contain saturated carboxylic acid such as formic acid, acetic acid, propionic acid and butyric acid as an impurity. When a water absorbent resin is produced by polymerizing an acrylic acid (salt) containing the saturated carboxylic acid, the saturated carboxylic acid remain in the water absorbent resin in an amount of 10% to 100% by weight, particularly 50% to 100% by weight, depending on the production process, and therefore, there is a possibility that unpleasant odor such as an acid odor may occur in the water absorbent resin.

Thus, from the viewpoint of preventing the unpleasant odor, a content of formic acid, acetic acid, propionic acid or butyric acid, preferably a total content of acetic acid and propionic acid, which have particularly strong unpleasant odors, is preferably adjusted to 1500 ppm or less, more preferably to 1000 ppm or less, and still more preferably 500 ppm or less, relative to the monomer(s) that include acrylic acid (salt) as a main component. The lower limit is not particularly limited and is 0 ppm or more (there is no particular problem even with 0 ppm). When the content of the saturated carboxylic acids is controlled to be equal to or less than the upper limit, a water absorbent resin in which an unpleasant odor (particularly, an acid odor) is suppressed can be obtained.

(d) Other Trace Component

The acrylic acid (salt) used in the present invention contains an impurity such as acrylic acid dimer, β-hydroxypropionic acid, protoanemonin, furfural, and maleic acid.

A content of the acrylic acid dimer in the monomer that include acrylic acid (salt) as a main component is, from the viewpoint of reducing an amount of residual monomers, preferably 2000 ppm or less, more preferably 1000 ppm or less, still more preferably 500 ppm or less, and particularly preferably 100 ppm or less. The lower limit is not particularly limited and may be 0 ppm or more (there is no particular problem even with 0 ppm).

A content of the β-hydroxypropionic acid in the monomers that include acrylic acid (salt) as a main component is, from the viewpoint of reducing a amount of residual monomers, preferably 1 ppm to 1000 ppm. Meanwhile, since β-hydroxypropionic acid gives the same effect irrespective of being in the acid form or in the salt form, a β-hydroxypropionic acid salt is also considered to be included in β-hydroxypropionic acid.

Also for the impurities such as protoanemonin, aldehydes such as furfural, and maleic acid, from the viewpoint of enhancing physical properties or water absorption characteristics of the resulting water absorbent resin, it is preferable to control the content thereof. Specifically, the content of the impurities are preferably adjusted respectively to less than 1 ppm.

(2-2) Polymerization Step

The present step is a step of obtaining a water-containing gel-like crosslinked polymer (hereinafter, also referred to as "water-containing gel") by polymerizing an aqueous monomer solution containing acrylic acid (salt) as a main component.

(a) Monomer (Excluding Crosslinking Agent)

The water absorbent resin obtainable in the present invention uses, as a raw material thereof, a monomer (s) that includes acrylic acid (salt) as a main component, in an aqueous solution form (hereinafter, also referred to as "aqueous monomer solution"). A monomer concentration in the aqueous monomer solution is not particularly limited. From the viewpoint of physical properties of the water absorbent resin thus obtainable, the monomer concentration is preferably 10% to 70% by weight, more preferably 15% to 65% by weight, and still more preferably 30% to 55% by weight.

A water-containing gel obtainable by polymerization of the aqueous monomer solution is preferably such that at least a portion of the acid groups in the polymer is neutralized, from the viewpoint of water absorption performance. The neutralization can be carried out before polymerization, during polymerization, or after polymerization. From the viewpoint of increasing the productivity of the water absorbent resin, improved AAP (absorption capacity under load) and SFC (saline flow conductivity), and the like, it is preferable to perform neutralization before polymerization. That is, it is preferable to use neutralized acrylic acid (that is, a partially neutralized salt of acrylic acid) as a monomer.

When the partially neutralized salt of acrylic acid is used as a monomer, a neutralization ratio is preferably equal to or more than 10% by mole and less than 90% by mole, more preferably equal to or more than 40% by mole and less than 80% by mole, still more preferably equal to or more than 50% by mole and less than 74% by mole, and particularly preferably equal to or more than 50% by mole and less than 72% by mole, with respect to the acid groups. When the neutralization ratio is adjusted to 10% by mole or more, a conspicuous decrease in CRC (absorption capacity without load) can be prevented. On the other hand, by adjusting the neutralization ratio to less than 90% by mole, a water absorbent resin having high AAP (absorption capacity under load) can be obtained. Even in the case of performing neutralization during polymerization or after polymerization, a preferred neutralization ratio with respect to the acid groups is as described above.

Furthermore, as the acrylic acid salt, monovalent salts of acrylic acid, such as alkali metal salts of lithium, sodium, potassium and the like, ammonium salts, and amine salts, are usually used, and the acrylic acid salt is preferably an alkali metal salt or an ammonium salt, and more preferably a sodium salt, a potassium salt, or an ammonium salt. That is, the acrylic acid salt is produced by neutralization reaction between acrylic acid and a basic substance, and regarding the basic substance, from the viewpoints of the performance and cost of the water absorbent resin thus obtainable, a basic substance capable of producing a sodium salt or an ammonium salt is preferred, and in particular, sodium hydroxide or ammonia is preferred. Furthermore, the neutralization reaction is not limited to being carried out for the monomers before polymerization (acrylic acid), and may also be carried out for the polymer obtained during polymerization or after polymerization. Moreover, neutralization of the monomer and neutralization of the polymer may be carried out in combination, but preferably, acrylic acid as a monomer component is subjected to neutralization reaction. In this case, a preferred neutralization ratio of acrylic acid is in the range described above with respect to the acid groups. Also, a polyvalent metal salt such as a calcium salt or an aluminum salt may also be used in combination, as long as the water absorbent resin is water-swellable.

In the present invention, when an acrylic acid ammonium salt is used, if only the ammonium salt is used, a preferred neutralization ratio is in the range described above, and if another salt is used in combination therewith, it is preferable that the acrylic acid ammonium salt be included in an amount of 1% by mole or more, and more preferably 5% by mole or more, relative to the total amount of monomer. That is, ammonium acrylate is preferably included in the aqueous monomer solution containing acrylic acid (salt) as a main component, in an amount of equal to or more than 1% by mole and less than 90% by mole, and more preferably in an amount of equal to or more than 5% by mole and less than 90% by mole, relative to the total amount of monomer.

Furthermore, a temperature in the neutralization (neutralization temperature) is not particularly limited, and is preferably 10° C. to 100° C., and more preferably 30° C. to 90° C. Meanwhile, in regard to neutralization treatment conditions other than those described above, the conditions disclosed in WO 2006/522181, and the like are preferably applied to the present invention.

In the present invention, a monomer other than acrylic acid (salt) may also be used in combination. There are no particular limitations on the monomer other than acrylic acid (salt) that is used in combination.

(b) Internal Crosslinking Agent

In the present invention, from the viewpoint of water absorption performance of the water absorbent resin thus obtainable, it is preferable to use a crosslinking agent (hereinafter, also referred to as an "internal crosslinking agent"). The crosslinking method is not particularly limited, but examples include a method of adding a crosslinking agent during polymerization or after polymerization and then performing post-crosslinking; a method of performing radical crosslinking by using a radical polymerization initiator; a method of performing radiation crosslinking by using an electron beam or the like; and the like. Among them, a method of adding a predetermined amount of an internal crosslinking agent in advance to a monomer, subsequently performing polymerization, and carrying out crosslinking reaction simultaneously with polymerization or after polymerization is preferred.

Examples of the internal crosslinking agent that can be used in the present invention include N,N'-methylenebisacrylamide, (poly)ethylene glycol di(meth)acrylate, (poly)propylene glycol di(meth)acrylate, (polyoxyethylene) trimethylolpropane tri(meth)acrylate, (polyoxyethylene) glycol tri(meth)acrylate, trimethylolpropane di(meth)acrylate, polyethylene glycol di($\beta$-acryloyloxypropionate), trimethylolpropane tri($\beta$-acryloyloxypropionate), poly(meth)allyloxyalkane, polyethylene glycol diglycidyl ether, ethylene glycol, propylene glycol, glycerin, butanediol, erythritol, xylytol, sorbitol, polyethylene glycol, and the like. One kind or two or more kinds of these internal crosslinking agents are used. Meanwhile, in consideration of water absorption characteristics of the water absorbent resin thus obtainable, it is preferable to use a compound having two or more polymerizable unsaturated groups in the polymerization.

A used amount of the internal crosslinking agent is preferably 0.005% to 2% by mole, more preferably 0.01% to 1% by mole, and still more preferably 0.05% to 0.2% by mole, relative to the monomer(s). When the used amount of the internal crosslinking agent is adjusted within the range described above, excellent water absorption characteristics can be exhibited.

(c) Other Components

For the purpose of improving physical properties of the water absorbent resin of the present invention, a water-soluble resin or a water absorbent resin such as starch, polyacrylic acid (salt), polyvinyl alcohol, and polyethyleneimine can be added to the aqueous monomer solution in an amount of 0% to 50% by weight, preferably 0% to 20% by weight, and more preferably 0% to 10% by weight, relative to the monomer(s). Furthermore, physical properties of the water absorbent resin can also be improved by adding an additive such as various foaming agents (carbonates, azo compounds, air bubbles, and the like), surfactants, chelating agents and chain transfer agents in an amount of 0% to 5% by weight, and preferably 0% to 1% by weight, relative to the monomer(s). Furthermore, use of the water-soluble resin or water absorbent resin results in a graft polymer or a water absorbent resin composition. In the present invention, a starch-acrylic acid polymer, a PVA-acrylic acid polymer and the like are also collectively referred to as a polyacrylic acid (salt)-based water absorbent resin.

(d) Polymerization Method

In the polymerization step of the present invention, from the viewpoint of water absorption performance of a water absorbent resin, easy polymerization control, or the like, aqueous solution polymerization or reverse phase suspension polymerization is usually employed, but preferably, aqueous solution polymerization, more preferably continuous aqueous solution polymerization, is employed. Furthermore, preferred forms of the aqueous solution polymerization include continuous belt polymerization (disclosed in U.S. Pat. No. 4,893,999, U.S. Pat. No. 6,241,928, US Published Patent Application No. 2005/215734, and the like), continuous or batch kneader polymerization (disclosed in U.S. Pat. No. 6,987,151, U.S. Pat. No. 6,710,141, and the like), and the like, and among these, continuous belt polymerization is particularly preferred. When aqueous solution polymerization or reverse phase suspension polymerization is employed, a solvent other than water may be used in combination as necessary, and the kind of the solvent that is used in combination is not particularly limited.

Meanwhile, the aqueous solution polymerization is a method of polymerizing an aqueous monomer solution without using a dispersing solvent, and is disclosed in, for example, United States patents such as U.S. Pat. Nos. 4,625,001, 4,873,299, 4,286,082, 4,973,632, 4,985,518, 5,124,416, 5,250,640, 5,264,495, 5,145,906, and 5,380,808; and European patents such as European Patent Nos. 0811636, 0955086, 0922717, 1178059, 1711541, and 1799721. The monomers, crosslinking agents, polymerization initiators, and other additives that are disclosed in these patents can also be applied to the present invention.

Furthermore, the reverse phase suspension polymerization is a method of performing polymerization by suspending an aqueous monomer solution in a hydrophobic organic solvent, and is disclosed in, for example, United States patents such as U.S. Pat. Nos. 4,093,776, 4,367,323, 4,446, 261, 4,683,274, and 5,244,735.

When the aqueous monomer solution is subjected to aqueous solution polymerization or reverse phase suspension polymerization, the polymerization can be carried out in an air atmosphere, but preferably, the polymerization is carried out in an inert gas atmosphere of nitrogen, argon or the like (for example, in which an oxygen concentration is 1% by volume or less). That is, it is preferable to perform polymerization after dissolved oxygen in monomer components is sufficiently replaced with an inert gas (for example, an oxygen concentration is less than 1 [mg/L]). Also, the polymerization can be carried out at any pressure as of under reduced pressure, normal pressure, and increased pressure.

Furthermore, a size of a polymerization apparatus can be appropriately determined, but in order to exhibit effects by the present invention more effectively, the present method advantageously applied when a water absorbent resin is produced in a large scale (actual production scale). In that case, the size of polymerization apparatus is, for example, as a production per hour per polymerization apparatus, preferably 100 [kg/hr] or larger, more preferably 500 [kg/hr] or larger, and still more preferably 1000 [kg/hr] or larger. Furthermore, the size is also suitable for continuous production including a drying step and a surface crosslinking step. Furthermore, in regard to the production per hour, the upper limit is not particularly limited, but from the viewpoint of physical properties of the water absorbent resin thus obtainable, the upper limit is preferably about 100 [t/hr], and more preferably about 500 [t/hr].

(2-3) Gel Fine Granulation Step

The water-containing gel obtained by the polymerization is crushed by using a gel crusher (a kneader, a meat chopper, a cutter mill or the like) as necessary, and is converted to a particulate form (hereinafter, also referred to as "particulate water-containing gel"). That is, a step for fine granulation of a water-containing gel (hereinafter, also referred to as "gel crushing") may be further included between a polymerization step based on continuous belt polymerization or continuous kneader polymerization and a drying step.

(2-4) Drying Step

In regard to the drying method of the present invention, any method capable of drying a water-containing gel obtained by the polymerization step or a particulate water-containing gel obtained by the gel fine granulation step to a desired resin solid content may be used, and there are no particular limitations on the mode. For example, various methods such as drying by heating, hot air drying, drying under reduced pressure, fluidized bed drying, infrared drying, microwave drying, drum dryer drying, dehydration by azeotropic boiling with a hydrophobic organic solvent, and high humidity drying using steam at a high temperature, can be employed.

Among these, hot air drying is preferred, hot air drying by a gas having a dew point temperature of 40° C. to 100° C. is more preferred, and hot air drying by a gas having a dew point temperature of 50° C. to 90° C. is still more preferred.

In the present invention, a drying temperature that can be applied is not particularly limited, but it is preferably 50° C. to 300° C. (in the case of 100° C. or lower, it is preferable to perform drying under reduced pressure), more preferably 100° C. to 250° C., and still more preferably 150° C. to 200° C. Furthermore, a drying time is preferably 10 minutes to 120 minutes, more preferably 20 minutes to 90 minutes, and still more preferably 30 minutes to 60 minutes. When the drying time is adjusted to equal to or longer than the lower limit, the polymer chain in the water absorbent resin changes, the absorption capacity is increased, and a sufficient effect of improving absorption capacity under load and the like can be obtained by surface crosslinking step that will be described below. On the other hand, when the drying time is adjusted to be equal to or shorter than the upper limit, damage to a water absorbent resin is suppressed, to prevent increase in water extractable content. Thereby, various physical properties of water absorbent resin can be enhanced.

(2-5) Pulverization Step and Classification Step

The present steps are a step of obtaining a particulate water absorbent resin by pulverizing and classifying a dried polymer obtained by the drying step.

A dried polymer is obtained by drying the water-containing gel after polymerization, and this dried polymer can be used directly as a dry powder (preferably, having a solid content of 80% by weight or more). However, for enhancement of physical properties by surface crosslinking that will be described below, the dried polymer is preferably adjusted to a specific particle size. The particle size adjustment of water absorbent resin can be appropriately carried out at any arbitrary step such as a polymerization step, a granulation step or a fine powder collection step, without being limited to pulverization step and classification step. Hereinafter, the particle size will be defined by means of standard sieves (JIS Z8801-1 (2000)). Also, in the case where the present method comprises a surface crosslinking step, the same classification step may be disposed before and after the surface crosslinking step. In this case, the classification step before the surface crosslinking step (after the drying step) is referred to as a first classification step, and the classification step after the surface crosslinking step is referred to as a second classification step.

From the viewpoint of enhancing physical properties of the water absorbent resin obtainable by the present invention, it is preferable to control a particle size so as to give a particle size described below. That is, D50 (weight average particle size) of the water absorbent resin before surface crosslinking is preferably 200 μm to 600 μm, more preferably 200 μm to 550 μm, still more preferably 250 μm to 500 μm, and particularly preferably 350 μm to 450 μm. Furthermore, a proportion of fine particles that pass through a sieve having a mesh size of 150 μm (JIS standard sieve) is preferably 0% to 5% by weight, more preferably 0% to 3% by weight, and still more preferably 0% to 1% by weight, relative to the total amount of the water absorbent resin. Furthermore, a proportion of large particles that do not pass through a sieve having a mesh size of 850 μm (JIS standard sieve) is preferably 0% to 5% by weight, more preferably 0% to 3% by weight, and still more preferably 0% to 1% by weight, relative to the total amount of the water absorbent resin. Also, in the present invention, preferably a proportion of particles having a particle size of equal to or larger than 150 μm and less than 850 μm, and more preferably a proportion of particles having a particle size of equal to or larger than 150 μm and less than 710 μm, is preferably 95% by weight or more, and more preferably 98% by weight or more (the upper limit is 100% by weight). Furthermore, a logarithmic standard deviation of particle size distribution ($\sigma\zeta$) is preferably 0.25 to 0.45, more preferably 0.30 to 0.40, and still more preferably 0.32 to 0.38. These particle sizes are measured by the method disclosed in WO 2004/69915 or EDANA-ERT420.2-02. The particle size before surface crosslinking is applied also to a particle size after surface crosslinking, and to a particle size of a final product. Meanwhile, if the particle size is out of the range described above, there would be a risk that segregation of particles may occur even during a storage period according to the present invention, and a decrease or deflection of physical properties of the water absorbent resin may occur.

(2-6) Fine Powder Recycling Step

The present step is a step of separating a fine powder (particularly a fine powder containing powder particles having a particle size of 150 μm or less at a proportion of 70% by weight or more) that is generated in the drying step, and optionally the pulverization step and the classification step, and then recycling the fine powder to the polymerization step, the drying step or the like in an unchanged state or in a hydrated state. By carrying out the fine powder recycling step, control of particle size, and improvement of water absorption speed or liquid permeability can be attained. An amount of the fine powder recycled is appropriately determined in the range of usually 0.1% to 40% by weight, preferably 1% to 30% by weight, and more preferably 5% to 25% by weight, relative to the total amount of the fine powder.

(2-7) Surface Crosslinking Step

The present step is a step of crosslinking a vicinity of a surface of water absorbent resin obtained from the pulverization step and the classification step for improvement of water absorption performance, by using a surface crosslinking agent (surface crosslinking reaction). Through the surface crosslinking, a water absorbent resin which is more suitable for the use in hygienic materials can be obtained. The surface crosslinking may be carried out simultaneously with drying, but is preferably carried out after the drying step, and more preferably after the classification step. Meanwhile, the "surface crosslinking" is to provide an area with a higher crosslinking density in a surface layer of the water absorbent resin (usually about several ten micrometers (μm)

from a surface of water absorbent resin), which can be formed by radical surface crosslinking, surface polymerization on the surface (which forms a crosslinked layer by polymerization of monomers or a crosslinking agent), a crosslinking reaction with a surface crosslinking agent, or the like.

The surface crosslinking agent that can be used in the present invention is not particularly limited, but various organic crosslinking agents or inorganic crosslinking agents may be used. Among them, from the viewpoints of physical properties and easy handling, a crosslinking agent capable of reacting with a carboxyl group can be preferably used. For example, a ring-opening reactive crosslinking agent such as polyvalent epoxy compounds or polyvalent aziridine compounds; or a dehydration reactive crosslinking agent (a surface crosslinking agent having a hydroxyl group, an amino group or a derivative thereof) such as polyhydric alcohol compounds, oxazoline compounds, mono-, di-, or polyoxazolidinone compounds, alkylene carbonate compounds, oxetane compounds, and cyclic urea compounds can be suitably used. Furthermore, an ion-reactive crosslinking agent such as polyvalent metal salts and polyamines may also be used in combination.

Meanwhile, the dehydration reactive crosslinking agent refers to a crosslinking agent which allows dehydration esterification reaction or dehydration amidation reaction between a carboxyl group of a water absorbent resin and a functional group (for example, a hydroxyl group, an amino group, or the like) of a crosslinking agent. A crosslinking agent capable of producing a hydroxyl group after undergoing ring-opening reaction with a carboxyl group, and performing dehydration esterification reaction or dehydration amidation reaction, such as an alkylene carbonate compound, is also included.

There are no particular limitations on the surface crosslinking agent, but more specifically, the compounds exemplified in U.S. Pat. No. 6,228,930, U.S. Pat. No. 6,071,976, U.S. Pat. No. 6,254,990 and the like may be used. Examples thereof include polyhydric alcohol compounds such as mono-, di-, tri-, tetra- or polyethylene glycol, monopropylene glycol, 1,3-propanediol, dipropylene glycol, 2,3,4-trimethyl-1,3-pentanediol, polypropylene glycol, glycerin, polyglycerin, 2-butene-1,4-diol, 1,4-butanediol, 1,3-butanediol, 1,5-pentanediol, 1,6-hexanediol, and 1,2-cyclohexanedimethanol; epoxy compounds such as ethylene glycol diglycidyl ether and glycidol; polyvalent amine compounds such as ethylenediamine, diethylenetriamine, triethylenetetramine, tetraethylenepentamine, pentaethylenehexamine, polyethyleneimine, and polyamide polyamine; haloepoxy compounds such as epichlorohydrin, epibromohydrin, and α-methylepichlorohydrin; condensates between the polyvalent amine compounds and the haloepoxy compounds; oxazolidinone compounds such as 2-oxazolidinone; alkylene carbonate compounds such as ethylene carbonate; oxetane compounds; cyclic urea compounds such as 2-imidazolidinone; and the like. Among these, it is preferable to use one kind or two or more kinds of polyhydric alcohol compounds, oxazolidinone compounds and alkylene carbonate compounds.

Furthermore, an ion-reactive crosslinking agent (a crosslinking agent capable of ionic reaction with a carboxyl group of a water absorbent resin) such as a polyvalent metal salt or a polyamine polymer may be used in combination, and for example, a polyvalent metal salt as described below may be added simultaneously with or separately from the surface crosslinking agent (particularly, a dehydration reactive crosslinking agent), and be used in combination.

Furthermore, in order to solve the problems, among the surface crosslinking agents described above, it is preferable to use a surface crosslinking agent other than an epoxy surface crosslinking agent (a polyvalent epoxy compound). It is because when an epoxy surface crosslinking agent is used as a main component, and particularly when only an epoxy surface crosslinking agent is used, there would a possibility that problems may occur in safety due to residual crosslinking agent. In view of absorption capacity under load under high load (AAP 0.7 psi) or liquid permeability under load (SFC), it is more preferable to use a dehydration reactive crosslinking agent as an essential ingredient.

In the case of using the epoxy surface crosslinking agent and the dehydration reactive crosslinking agent in combination, an amount of the epoxy surface crosslinking agent used is reduced to an amount as small as preferably 0% to 20% by weight, and more preferably 0% to 10% by weight, relative to the dehydration reactive crosslinking agent. Thereby, an amount of residual epoxy surface crosslinking agent can be lowered to below a detection limit (ND).

As described above, remaining epoxy surface crosslinking agent has a problem also in view of safety, and Patent Document 16 (U.S. Pat. No. 5,981,070) discloses a method for reducing a residual epoxy surface crosslinking agent by adding water and leaving the system to stand at room temperature, after the use of an epoxy surface crosslinking agent (claims 37 to 39 and Example 17). However, such a patent document does not disclose control of an amount of residual monomers and an amount of Fe that is essential in the present invention, or other constitution.

An amount of surface crosslinking agent used may vary depending on a compound used or a combination of such compounds. It is preferably 0.001 parts to 10 parts by weight, and more preferably 0.01 parts to 5 parts by weight, relative to 100 parts by weight of water absorbent resin. According to the present invention, water can be used in combination with the surface crosslinking agent. At this time, an amount of water used is preferably 0.5 parts to 20 parts by weight, and more preferably 0.5 parts to 10 parts by weight, relative to 100 parts by weight of water absorbent resin. Furthermore, in the present invention, a hydrophilic organic solvent other than water can also be used.

In this case, an amount of hydrophilic organic solvent used is preferably 0 parts to 10 parts by weight, and more preferably 0 parts to 5 parts by weight, relative to 100 parts by weight of water absorbent resin. Also, in the mixing a surface crosslinking agent solution into a water absorbent resin, a water-insoluble fine particulate powder or a surfactant may also be incorporated to an extent that effects by the present invention is not impaired, for example, in an amount of 0% to 10% by weight or less, preferably 0% to 5% by weight, and more preferably 0% to 1% by weight. The surfactant to be used and the used amount thereof are disclosed in U.S. Pat. No. 7,473,739.

The surface treatment in the method for producing a water absorbent resin of the present invention is a surface crosslinking reaction step for increasing a crosslinking density in a surface of water absorbent resin, and a water absorbent resin after a surface crosslinking agent has been incorporated is preferably subjected to heat-treatment and if necessary, subjected to cooling thereafter. A heating temperature is usually 70° C. to 300° C., preferably 120° C. to 250° C., and more preferably 150° C. to 250° C. When the heating temperature is adjusted to be equal to or higher than the lower limit, surface crosslinking of a water absorbent resin is caused to proceed sufficiently, and absorption capacity under load or saline flow conductivity can be increased. On the other hand, when the heating temperature is adjusted to be equal to or lower than the upper limit, coloration of a water absorbent resin can be prevented. Furthermore, a heating time is preferably in the range of 1 minute to 2 hours. Meanwhile, the heat-treatment can be carried out by using a conventional dryer or heating furnace.

(2-8) Addition Step

The present invention preferably further includes, in order to prevent aggregation and/or coloration of a water absorbent resin during or after a packaging step and storage step which will be described below, a step of adding to the water absorbent resin at least one or more aggregation preventing agents selected from the group consisting of polyvalent metal salts, water-insoluble fine particles and surfactants, and/or at least one or more coloration preventing agents selected from the group consisting of α-hydroxycarboxylic acid compounds, inorganic reducing agents and chelating agents, during or before the packaging step.

The addition step of the aggregation preventing agent and/or coloration preventing agent is provided between the polymerization step and the surface crosslinking step, or thereafter, and the aggregation preventing agent and/or the coloration preventing agent is preferably added in the form of an aqueous solution. By adding the agents as aqueous solutions, a moisture content of the water absorbent resin can also be simultaneously controlled within a predetermined range. Hereinafter, the aggregation preventing agent and the coloration preventing agent will be described in order.

(a) Aggregation Preventing Agent (Polyvalent Metal Salt)

The water absorbent resin of the present invention preferably contains a polyvalent metal salt, from the viewpoints of prevention of aggregation, increase in liquid permeability (SFC), and the like. It is preferable that the polyvalent metal salt be present on the surface of the water absorbent resin in view of effects thereby, and therefore, it is preferable that the addition step be carried out simultaneously with or after the surface crosslinking.

The polyvalent metal salt in the present invention is an organic acid salt or inorganic acid salt of a polyvalent metal, and polyvalent metal salts such as aluminum, zirconium, iron, titanium, calcium, magnesium, and zinc are preferred. The polyvalent metal salt may be any of a water-soluble salt or a non-water-soluble salt; however, a water-soluble polyvalent metal salt is preferred, and a water-soluble polyvalent metal salt which dissolves in water at 25° C. in an amount of 2% by weight or more, and preferably 5% by weight or more, can be suitably used. Specific examples thereof include inorganic acid salts such as aluminum chloride, polyaluminum chloride, aluminum sulfate, aluminum nitrate, potassium aluminum bissulfate, sodium aluminum bissulfate, potassium alum, ammonium alum, sodium alum, sodium aluminate, calcium chloride, calcium nitrate, magnesium chloride, magnesium sulfate, magnesium nitrate, zinc chloride, zinc sulfate, zinc nitrate, zirconium chloride, zirconium sulfate, and zirconium nitrate; and organic acid salts such as lactates and acetates of the polyvalent metals. Furthermore, from the viewpoint of solubility in an absorbed liquid such as urine, it is preferable to use a salt having crystallization water.

In particular, aluminum compounds, among others, aluminum chloride, polyaluminum chloride, aluminum sulfate, aluminum nitrate, potassium aluminum bissulfate, sodium aluminum bissulfate, potassium alum, ammonium alum, sodium alum, and sodium aluminate are preferred, and aluminum sulfate is particularly preferred, while a powder in a crystallization water form such as aluminum sulfate octadecahydrate, aluminum sulfate tetradeca- to octadeca-hydrate and the like can be most suitably used. These may be used singly, or two or more kinds may be used in combination.

An amount of the polyvalent metal salt contained in the water absorbent resin of the present invention is preferably 0 parts to 5 parts by weight, more preferably 0.001 parts to 3 parts by weight, and still more preferably 0.01 parts to 2 parts by weight. When the amount of the polyvalent metal salt is adjusted to be equal to or less than the upper limit, a conspicuous decrease in absorption performance, particularly absorption capacity, or coloration can be prevented.

(Water-Insoluble Fine Particles)

In the present invention, water-insoluble inorganic or organic fine particles (also referred to as "water-insoluble fine particles") are preferably added to the water absorbent resin. When water-insoluble inorganic or organic fine particles are present particularly on the surface of the water absorbent resin, physical properties can be further enhanced or stabilized. The water-insoluble fine particles are preferably added to the water absorbent resin obtained after the drying step, and preferably to the water absorbent resin obtained before and after or during (simultaneously) the surface crosslinking step.

As the water-insoluble organic fine particles, examples include organic acid salts of polyvalent metals having 7 or more carbon atoms, metal soaps and the like disclosed in U.S. Pat. No. 7,282,262 or the like. Furthermore, examples of the water-insoluble inorganic fine particles that can be used are disclosed in U.S. Pat. No. 7,638,570 and the like, and preferably, fine particles having a volume average particle size of 10 μm or less, more preferably 1 μm or less, and particularly preferably 0.1 μm or less, are used. Specifically, silica ($SiO_2$), kaolin, talc and the like can be used, but there are no particular limitations thereto. An amount of the water-insoluble fine particles to be added is preferably 0 parts to 1 part by weight, more preferably 0.0001 parts to 0.5 parts by weight, and still more preferably 0.001 parts to 0.1 parts by weight, relative to 100 parts by weight of the water absorbent resin. When the amount of the water-insoluble fine particle to be added is adjusted to be equal to or less than the upper limit, cost can be lowered, and also, increase in a re-wet amount in a paper diaper can be prevented.

(Surfactant)

In the present invention, a surfactant is preferably added to the water absorbent resin. When the surfactant is present on the surface of the water absorbent resin, physical properties can be further enhanced or stabilized. The surfactant is preferably added to the water absorbent resin obtained after the drying step, more preferably to the water absorbent resin obtained before or after, or during (simultaneously) the surface crosslinking step, particularly simultaneously with or after the incorporation of a cationic polymer.

Examples of the surfactant include those disclosed in U.S. Pat. No. 6,107,358 and the like. Furthermore, an amount of the surfactant to be added is preferably 0 parts to 1 part by weight, more preferably 0.0001 parts to 0.5 parts by weight, and still more preferably 0.001 parts to 0.1 parts by weight, relative to 100 parts by weight of the water absorbent resin. When the amount of the surfactant to be added is adjusted to be equal to or less than the upper limit, cost can be lowered, and also, increase in a re-wet amount in a paper diaper due to a decrease in surface tension of the water absorbent resin can be prevented. Particularly, in order to maintain a powder state in a predetermined package amount under conditions of a moisture content that will be described below, particularly under conditions of a moisture content higher than a conventional moisture content, preferably, at least one or more members selected from the group consisting of polyvalent metals, water-insoluble fine particles, and surfactants are preferably added to the water absorbent resin.

(b) Coloration Preventing Agent (α-Hydroxycarboxylic Acid Compound)

In the present invention, an α-hydroxycarboxylic acid compound is preferably added to the water absorbent resin, in view of further prevention of coloration or the like. The α-hydroxycarboxylic acid compound according to the present invention means a carboxylic acid having a hydroxyl group at the α-position of the carboxyl group, or a salt thereof. It is preferable, in view of the effects, that the α-hydroxycarboxylic acid compound be present in the interior or on the surface of the water absorbent resin.

The α-hydroxycarboxylic acid compound is preferably a non-polymeric α-hydroxycarboxylic acid compound. Particularly, from the viewpoints of easy addition and effects by the addition, a molecular weight of the α-hydroxycarboxylic acid compound is preferably 40 to 2000, more preferably 60 to 1000, and still more preferably 100 to 500, and it is preferable to use a water-soluble α-hydroxycarboxylic acid compound. Examples of the α-hydroxycarboxylic acid compound include glycolic acid, tartaric acid, lactic acid (salt), citric acid (salt), malic acid (salt), isocitric acid (salt), glyceric acid (salt), poly-α-hydroxyacrylic acid (salt), and the like. Among them, lactic acid (salt) and malic acid (salt) are preferred, and lactic acid (salt) is more preferred.

An amount of the α-hydroxycarboxylic acid compound to be added is preferably 0.05% to 1.0% by weight, more preferably 0.05% to 0.5% by weight, and still more preferably 0.1% to 0.5% by weight, relative to the water absorbent resin, from the viewpoint of cost performance.

(Inorganic Reducing Agent)

In the production method of the present invention, from the viewpoints of further prevention of coloration or prevention of deterioration, and reduced amount of residual monomers, a step of adding an inorganic reducing agent to the water absorbent resin may be included.

Examples of the inorganic reducing agent in the present invention include an inorganic reducing agent containing a sulfur atom, and an inorganic reducing agent containing a phosphorus atom. The inorganic reducing agent may be in an acid form, but is preferably in a salt form, and the salt is preferably a monovalent salt or a polyvalent metal salt, and more preferably a monovalent salt. Suitable examples of the inorganic reducing agent are described in US Published Patent Application No. 2006/074160, and (hydrogen) sulfites and the like are preferably used.

An amount of the inorganic reducing agent to be added is preferably 0.001% to 1.5% by weight, more preferably 0.005% to 1.0% by weight, and still more preferably 0.01% to 0.5% by weight, relative to the water absorbent resin. When the amount of the inorganic reducing agent to be added is adjusted to be equal to or more than the lower limit, coloration over time of the water absorbent resin can be prevented. On the other hand, when the amount of the inorganic reducing agent to be added is adjusted to be equal to or less than the upper limit, foul odor of the water absorbent resin can be reduced, and particularly, the water absorbent resin can be prevented from increasing foul odor after absorbing an aqueous liquid.

It is preferable that the inorganic reducing agent be present in the interior or on the surface of the water absorbent resin, from the viewpoint of exhibiting its effect. Therefore, the addition step can be carried out at any stage during the production process. Specifically, the addition step can be carried out before or after, or simultaneously with the polymerization step (for example, added to the water-containing gel during polymerization); the gel fine granulation step after polymerization; the surface crosslinking step or cooling step thereafter; and the granulation step. Among others, in the present invention, the inorganic reducing agent is preferably added after the surface crosslinking treatment step from the viewpoint of reducing foul odor. When the inorganic reducing agent is added after the surface crosslinking treatment step, unpleasant odor in the water absorbent resin thus obtained, especially unpleasant odor generated after the water absorbent resin thus obtained has absorbed an aqueous liquid, can be suppressed. Such foul odor is not limited to a simple foul odor of the inorganic reducing agent, and is believed to be foul odor generated in the surface crosslinking step, particularly surface crosslinking step carried out for the purpose of increasing SFC or increasing AAP.

(Chelating Agent)

In the production method of the present invention, from the viewpoint of further preventing coloration or preventing deterioration, a chelating agent addition step may be included. It is preferable that the chelating agent be present in the interior or on the surface of the water absorbent resin, from the viewpoint of exhibiting its effect. Therefore, the addition step can be carried out, for example, before or after, or simultaneously with the polymerization step (specifically, added to a monomer in the polymerization or to the water-containing gel during polymerization); the gel fine granulation step after polymerization; the surface crosslinking step or cooling step thereafter; and the granulation step.

As the chelating agent of the present invention, a polymeric or non-polymeric chelating agent can be used without any limitation; however, from the viewpoint of its effect, it is preferable to use a non-polymeric chelating agent among others, and the chelating agent is more preferably a non-polymeric compound selected among polyvalent aminocarboxylic acid, organic polyvalent phosphoric acid and polyvalent aminophosphoric acid. Suitable examples of the chelating agent are disclosed in European Patent No. 940148.

A molecular weight of the chelating agent is preferably 100 to 5000, and more preferably 200 to 1000, from the viewpoint of its effect. Here, the term "polyvalent" is referred to a compound having plural functional groups in one molecule, and the number of functional groups in one molecule is preferably 2 to 30, more preferably 3 to 20, and still more preferably 4 to 10.

An amount of the chelating agent to be added is preferably 0.001% to 0.1% by weight, more preferably 0.002% to 0.05% by weight, still more preferably 0.003% to 0.04% by weight, and particularly preferably 0.004% to 0.02% by weight, relative to the water absorbent resin. When the amount of the chelating agent to be added is adjusted to be equal to or more than the lower limit, coloration over time of the water absorbent resin can be prevented. On the other hand, when the amount of the chelating agent to be added is adjusted to be equal to or less than the upper limit, deterioration of initial color tone of the water absorbent resin can be prevented.

(c) Other Additives

In the present invention, in order to impart various functions depending on a purpose, an organic powder of a compound containing a phosphorus atom, an oxidizing agent, an organic reducing agent, a metal soap or the like; a deodorizing agent, an antibacterial agent, pulp, a thermoplastic fiber or the like may be added to the water absorbent resin in an amount of preferably 0% to 3% by weight, and more preferably 0% to 1% by weight.

(2-9) Moisture Content Adjustment Step

In order to solve the problems of the present invention, a moisture content (amount of water) of the water absorbent resin in the packaging is controlled to be essentially 1% by weight or more, preferably 3% to 20% by weight, more preferably 5% to 20% by weight, still more preferably 7% to 20% by weight, particularly preferably 10% to 20% by weight, and most preferably 10% to 15% by weight.

Regarding a method for controlling a moisture content of the water absorbent resin, a method of controlling a reaction temperature or time in the surface crosslinking step (specifically, a method of completing the surface crosslinking reaction at a predetermined moisture content described above) or the like may be used, but in addition to that, a preferred embodiment may be a method of providing a moisture content adjustment step (addition of water; also called "rehumidification") after the surface crosslinking step. These plural moisture content adjustment steps may be used in combination. In the moisture content adjustment step after surface crosslinking, water (alone), or an aqueous solution or an aqueous dispersion liquid is added to the water absorbent resin after surface crosslinking, so as to give a moisture content described above. The water may be a solid (ice), a gas (steam), or a liquid, and water is heated or cooled as necessary at a temperature in the range of 0° C. to 150° C., and preferably 20° C. to 60° C.

The addition of water is preferably carried out simultaneously with the addition of various additives described above in an aqueous solution or an aqueous dispersion liquid form, and at that time, granulation of a fine powder by addition of water may also be carried out simultaneously, or if necessary, an amount of water in the water absorbent resin may also be adjusted by drying or heating after the addition. An amount of water to be added can be appropriately determined depending on a moisture content of the water absorbent resin after surface crosslinking, or conditions for heating or drying after the addition of water. The amount of water to be added is preferably 0.1 parts to 50 parts by weight, more preferably 0.5 parts to 20 parts by weight, and still more preferably 1 part to 10 parts by weight, relative to 100 parts by weight of the water absorbent resin.

(2-10) Method for Controlling Phenolic Compound

As described in the above section (2-1), in the present invention, it is preferable to incorporate a predetermined amount of a phenolic compound into an aqueous monomer solution in the polymerization, or into a water absorbent resin.

It has been hitherto disclosed in WO 2003/051940 (hereinafter, referred to as "Patent Document 15") and the like that p-methoxyphenol is contained in a monomer in the polymerization. Furthermore, Non-Patent Document 1 (page 41, Table 5.2) discloses an amount of residual p-methoxyphenol in a water absorbent resins produced at eight production sites, A to H. However, these documents do not disclose an iron content, a moisture content, and a storage period. Furthermore, since the phenolic compound in the monomer is consumed by the polymerization step, the drying step or the like, a content of the compound changes between that in the monomer and that in the water absorbent resin. However, in Patent Document 15, there is no disclosure on the amount of p-methoxyphenol in the water absorbent resin thus obtained, and in Non-Patent Document 1, there is no disclosure on the amount of p-methoxyphenol in the monomer in the polymerization.

There are no particular limitations on a method for controlling the p-methoxyphenol content in the water absorbent resin obtainable in the present invention, and specific examples include a method of performing aqueous solution polymerization or reverse phase suspension polymerization of an aqueous monomer solution at a monomer concentration of 30% to 55% by weight containing acrylic acid (salt) in the monomers in an amount of 90% to 100% by mole in the polymerization step, by using 0.001% to 1% by mole of a radical polymerization initiator under conditions of a maximum temperature of 130° C. or lower and a polymerization time of 0.5 minutes to 3 hours; a method of performing neutralization by using a basic substance having an iron content of 0 ppm to 7 ppm in the neutralization step; a method of drying a particulate water-containing gel to a moisture content of 20% by weight or less at a drying temperature of 100° C. to 250° C. for a drying time of 10 minutes to 120 minutes in the drying step; and a method of incorporating 0.001 parts to 10 parts by weight of a surface crosslinking agent relative to 100 parts by weight of a particulate water absorbent resin after completion of the drying step, and subjecting the mixture to heat-treatment at 70° C. to 300° C. for 1 minute to 2 hours, in the surface crosslinking step. When these methods are carried out singly or in appropriate combinations, and preferably in combination of all the methods, the p-methoxyphenol content in the water absorbent resin thus obtainable can be controlled (preferably controlled to 5 ppm to 60 ppm).

[3] Packaging and Storage of Polyacrylic Acid (Salt)-Based Water Absorbent Resin The production method of the present invention has a feature in that a water absorbent resin produced as subjected to the polymerization step, drying step, surface crosslinking step and the like is packaged, and then the water absorbent resin in the packaged state is stored for a predetermined period in a storage place. The term "packaging", as used herein, refers to action of packing the water absorbent resin obtainable in the present invention in a container for shipment, and for convenience, the step of packaging is also referred to as a packaging step. Furthermore, the term "storage" means storing of the water absorbent resin in a state of being packed in a container for shipment, and for convenience, the step of storing is also referred to as a storage step.

(3-1) Packaging Step (a) Packaging Container (Container for Shipment)

A container for packaging the water absorbent resin of the present invention may be any container capable of leaving the water absorbent resin to stand for a long time, and there are no particular limitations. Examples thereof include paper containers such as a paper bag, corrugated cardboard, and TETRA PAK (registered trademark); plastic containers such as a flexible container bag, a container, a laminate film, a corrugated plastic, a blister pack, and a bubble wrap; glass containers such as PYREX (registered trademark); metallic containers such as a tank and a silo; and the like. Among these, a flexible container bag, a container, a paper bag, and a tank are preferred, and a flexible container bag is more preferred.

The flexible container bag and the like preferably have a double-layered structure which includes an inner bag part and an outer packaging part. A material that constitutes the inner bag part may be any material which can prevent leakage of the water absorbent resin, has moisture barrier properties, and does not easily generate static electricity, and preferably a material which does not easily cause dew condensation under temperature change. There are no particular limitations, but examples of the material include plastics such as polyethylene (PE), polypropylene (PP), polyethylene terephthalate (PET), and polyvinyl chloride (PVC); an aluminum laminate material, an aluminum deposition material; and the like. Furthermore, at the time of completion of packing of the water absorbent resin, in order to prevent incorporation of moisture from ambient atmosphere, the inner bag part is heat-sealed as necessary. Therefore, a material capable of being heat-sealed is preferred. In regard to a material that constitutes the outer packaging part, a woven fabric having excellent strength or the like is preferred, and there are no particular limitations as long as the material has the properties described above, but for example, polypropylene and the like may be used.

Meanwhile, a container such as a hopper that is disposed within the various steps described above and/or between the various steps is intended to store the water absorbent resin temporarily. Particularly, in a continuous process, since the water absorbent resin is continuously supplied and discharged, this does not apply to the packaging container (container for shipment) defined as described above.

The packaging container essentially has a structure which maintains a sealed state or a state close to being sealed, from the viewpoint of preventing water, moisture or the like from being incorporated from ambient atmosphere. Furthermore, from the viewpoint of maintaining standing stability in the packaging and storage, the packaging container preferably has a structure in which the bottom has a flat surface. Also, the packaging container is preferably equipped with a member which is capable of earthing the static electricity that is generated in the packing of the water absorbent resin.

(b) Packing Method and Conditions

A method for packing the water absorbent resin of the present invention in the packaging container is not particularly limited, but examples include a method of utilizing gravity that is effected on the water absorbent resin, that is, free fall of the water absorbent resin; a method of utilizing a transfer means such as a belt conveyor, a screw conveyor, a vibratory conveyor, a bucket elevator, and a pneumatic transport; and the like.

In the packing method utilizing free fall, if packing is completed all at once, uneven distribution of particle size occurs. That is, water absorbent resins having a small particle size are concentrated in the upper part, while water absorbent resins having a large particle size are concentrated in the lower part, so that an uneven distribution layer is formed. Thus, uneven distribution of the particle size can be alleviated by increasing the number of packing steps to several times. The number of packing steps is not particularly limited, but the number of packing steps is preferably 2 to 4 times, more preferably 2 to 3 times, and particularly preferably 2 times.

Furthermore, in the present invention, it is preferable to pack the water absorbent resin after the inside of the container for shipment is purged with dry air. The term "dry air", as used herein, means a gas (air or the like) having a dew point temperature of −10° C. or lower, and preferably −100° C. to −10° C. Through the purging with dry air, moisture absorption of the water absorbent resin can be suppressed, and aggregation or adhesion of the water absorbent resin can be suppressed. Therefore, the effects caused by vibration as described below can be enhanced. Furthermore, a temperature of the dry air (gas temperature) is preferably −10° C. to 100° C., more preferably 0° C. to 50° C., still more preferably 10° C. to 40° C., and particularly preferably 20° C. to 30° C.

Furthermore, when the container for shipment is vibrated during or after packing of the water absorbent resin, an amount of air present between the particles of the water absorbent resin can be reduced, and uneven distribution of particle size is suppressed, which is preferable.

A packing rate employed when the water absorbent resin of the present invention is packed in the container for shipment is not particularly limited, but the packing rate is preferably 500 [kg/hr] or greater, and more preferably 1000 [kg/hr] or greater. Furthermore, a packing ratio is preferably 30% to 100% by volume, more preferably 50% to 99% by volume, and still more preferably 70% to 95% by volume. If the packing ratio is less than 30% by volume, packing efficiency would be low, and further there would be a risk that moisture in the air that has been entrained in the packing may cause formation of aggregates of the water absorbent resin, or deterioration of fluidity.

The container for shipment can be defined by a weight of the water absorbent resin to be packed, also in view of the packing ratio. That is, a volume of the container for shipment to be used, though varying depending on its structure, is desirably such a volume to allow the container to pack preferably 15 kg or more, more preferably 100 kg or more, still more preferably 500 kg or more, and particularly preferably 800 kg or more, of the water absorbent resin per container. Meanwhile, if the packing amount per container is less than 15 kg, efficiency by shipment would be poor, stability of physical properties in a batch (or per one package unit) would be low, and physical properties would fluctuate in different batches or in different containers, which is not preferable.

On the other hand, there are no particular limitations on the upper limit, but if the packing amount per container is too large, there would be a risk that the water absorbent resin may be damaged due to its own weight. Therefore, the packing amount is preferably 100 t or less, and preferably in the following order of 50 t or less, 10 t or less, and 5 t or less, while 2 t or less is particularly preferred.

Meanwhile, in the packing of the water absorbent resin, from the viewpoint of reducing damage, an additive such as a lubricating agent may be added as necessary. In the present invention, when a packaging amount is set to a predetermined amount or more, it is preferable to adjust a moisture content to the predetermined range described above from the viewpoint of reducing an amount of residual monomers. Aggregation is likely to occur due to a load at a container bottom in the packing in a large amount such as 1 t, and therefore, it is preferable to use one or more members, and more preferably two or more members, selected among surfactants, water-insoluble inorganic or organic fine powders and polyvalent metals.

(3-2) Storage Step

The method for producing a polyacrylic acid (salt)-based water absorbent resin according to the present invention includes a polymerization step of polymerizing an aqueous monomer solution containing acrylic acid (salt) as a main component; a drying step of drying the water-containing gel-like crosslinked polymer obtained in the polymerization step; a surface crosslinking step of surface crosslinking the water absorbent resin that is being dried or has been dried; and a packaging step of packaging the surface crosslinked water absorbent resin. However, these production steps are connected by various conveyers (for example, a pneumatic conveyor) and are installed in substantially the same plant or in substantially the same premise. Furthermore, in the present invention, the production process for acrylic acid (particularly, a purification step for acrylic acid) is also connected via a pipeline and is installed in substantially the same plant or in substantially the same premise. Furthermore, it is also preferable that after the packaging step, a storage step for storing in the same place or in a different place be installed in substantially the same plant or in substantially the same premise.

The "storage step" in the present invention means that the water absorbent resin is packaged (sealed) in a packaging container in the packaging step, and the water absorbent resin in a packaged state is stored for a certain period in a warehouse or the like inside or outside the production plant for the water absorbent resin until the water absorbent resin is shipped to a user. As used herein, the term "inside the plant" means storage in substantially the same premise or substantially the same company (including a subsidiary company and a parent company), while the term "outside the plant" means an external apparatus (storage in a warehouse company or the like other than the water absorbent resin manufacturer). Here, in order to avoid the energy consumption ($CO_2$ emission) associated with transportation after packaging, damage to the water absorbent resin (generation of fine dust) caused by vibration during transportation, and segregation (or a decrease in other physical properties) of the water absorbent resin, it is more preferable if a travel distance of the water absorbent resin during the storage step is closer, and specifically, the travel distance is preferably 50 km or less, 10 km or less, 5 km or less, 1 km or less, and 0.5 km or less in this order. Particularly, it is preferable for the water absorbent resin to be within substantially the same premise as that of the manufacturing plant of the water absorbent resin, or within substantially the same company.

In other words, the storage step is preferably provided adjacently to the manufacturing plant (the whole production process in which the polymerization step through the packaging step are all substantially connected) of the water absorbent resin, and further from the viewpoint of reducing residual monomers, it is preferable to also provide an acrylic acid production process adjacently.

Meanwhile, in the case of connecting an acrylic acid production process and a process for producing the water absorbent resin, the process for producing the water absorbent resin may be connected to the whole production process for acrylic acid (vapor phase oxidation, collection, and purification by distillation or crystallization), but is preferably connected to a final acrylic acid purification step. Furthermore, a manufacturing plant of acrylic acid and a manufacturing plant of water absorbent resin are preferably installed in proximity to each other.

When a production process of acrylic acid and a production of the water absorbent resin are connected, and particularly connected via a pipeline, a distance is preferably set to 10 km or less, more preferably 5 km or less, still more preferably 1 km or less, and particularly preferably 0.5 km or less. Furthermore, the storage step of the water absorbent resin is also preferably provided within the range of distance described above from the production process of the water absorbent resin. In this case, the production processes may be connected by a belt conveyor or the like, or short distance transportation by a forklift, a truck and the like is also acceptable.

It has been conventionally known that a production process may include a storage step such as a hopper prior to a packaging step, or include transportation after packaging. In the present invention, when a storage step is included anywhere between a packaging step and shipment, an amount of residual monomers can be reduced. Furthermore, when the aforementioned acrylic acid ammonium salt is used as a monomer, the aforementioned inorganic reducing agent is used, or the aforementioned moisture content is applied, reduction of an amount of residual monomers can be promoted. Moreover, other physical properties may be stabilized by using methoxyphenols, a chelating agent, a surfactant, and water-insoluble fine particles as described above, or by means of storage conditions such as described below.

A storage period is essentially 3 days or more, preferably 3 to 100 days, more preferably 4 to 70 days, still more preferably 5 to 50 days, particularly preferably 8 to 40 days, and most preferably 10 to 35 days. When the storage period is within the range described above, the water absorbent resin can be stabilized in a state with a reduced amount of residual monomers as compared with that in the packaging, and other physical properties can be also stabilized, which is preferable. If the storage period is less than 3 days, an amount of residual monomers is still in the middle of reduction, and the value is not stabilized. Also, the absolute amount of the residual monomer concentration is also still large, and therefore, it is not preferable. Furthermore, when the storage period is 100 days or less, a possibility that coloration or aggregation of the water absorbent resin may occur can be lowered. Meanwhile, the storage period is defined such that a time point at which packaging of the water absorbent resin is completed and a container for shipment is closed by sealing is regarded as a starting point.

In the present invention, reduction of residual monomers can be attained by providing a storage step in which the water absorbent resin is stored for a predetermined period or longer as described above. On the other hand, regarding the raw material acrylic acid, when a storage time is shortened such as to the range described above, reduction of residual monomers can be attained.

In the present invention, a mechanism in which an amount of residual monomers can be reduced by providing a storage step for a predetermined period is not clearly understood, but the present inventors speculate that an amount of residual monomers is decreased when a carboxyl group (—COOH) and the like present in a polymer chain of the water absorbent resin, and acrylic acid ($CH_2$=CHCOOH) as a residual monomer undergo a Michael addition reaction, and the residual monomer is incorporated as a part of the water absorbent resin.

An amount of residual monomers of the water absorbent resin that has been subjected to the storage step is reduced by preferably 0.5% or more, more preferably 1% or more, still more preferably 2% or more, and particularly preferably 5% or more, relative to an amount of residual monomers in the packaging. There are no particular limitations on the upper limit, but the upper limit is preferably 30% or less, and more preferably 20% or less. This reduction of residual monomers is observed in the early phase of the storage period, and if the storage period is 3 days or longer, the residual monomers are stabilized in a state of having been reduced as compared with the time of packaging.

Furthermore, a moisture content of the water absorbent resin measured before the storage, during the storage, or after the storage is 1% by weight or more, preferably 3% to 20% by weight, more preferably 5% to 20% by weight, still more preferably 7% to 20% by weight, particularly preferably 10% to 20% by weight, and most preferably 10 to 15 by weight. It is known that when a moisture content increases, generally absorption capacity without load (CRC)

or absorption capacity under load (AAP) decreases. Thus, various techniques for increasing the absorption capacity have been investigated; however, if the moisture content exceeds 20% by weight, even if a technique known to increase the absorption capacity is applied, it may be difficult to obtain a water absorbent resin having a high absorption capacity. Furthermore, a change in moisture content, particularly increase in moisture content, during the storage is preferably 2% by weight or less, and more preferably 1% by weight or less. The moisture content change of more than 2% by weight would have a possibility that a moisture content may go beyond the preferred moisture content range, as well as coloration may occur, aggregates may be generated, and water absorption properties may change. Meanwhile, it is speculated that change in water absorption properties caused by change in moisture content results from change in moisture content of the water absorbent resin, and a consequent change in content of a polymer component that absorbs water. If the water absorbent resin is stored such that a moisture content does not change to a large extent, usually no change occurs in water absorption properties.

In order to maintain the moisture content in the range described above and to suppress any change in the moisture content, it is preferable to employ a storage method that will be described below.

(Temperature/Humidity)

In the present storage step, a container for shipment packed with the water absorbent resin is preferably stored in an atmosphere at a temperature of 0° C. to 60° C., preferably 0° C. to 50° C., more preferably 0° C. to 40° C., and still more preferably 0° C. to 35° C., and at a relative humidity of 10% to 90%, and preferably 15% to 85%. When sealability of the container for shipment is high, a temperature and relative humidity may be temporarily out of the ranges of temperature and relative humidity described above; however, in the case where a container for shipment has a structure with low sealability, it is important to maintain the temperature and relative humidity in the ranges described above in order to suppress any change in moisture content of the water absorbent resin. Furthermore, when the temperature exceeds 60° C., there would be a risk that coloration or aggregation of the water absorbent resin may be accelerated, to induce decrease in its product's value. Therefore, it is preferable to store the water absorbent resin indoors, where an air conditioner, a blower facility or a ventilation facility, which are all capable of controlling temperature and/or humidity, is provided.

(Storage Place)

The water absorbent resin packed in a container for shipment by the packaging step is preferably stored indoors. In such a case, since the water absorbent resin is not influenced by weather conditions such as wind, rain, and direct sunlight, better effects can be exhibited. Furthermore, it is more preferable to store the water absorbent resin in a warehouse equipped with an air conditioner. Also, from the viewpoint of damage of the water absorbent resin caused by vibration, it is preferable to leave the water absorbent resin to stand in a place with less vibration. Furthermore, from the viewpoint of damage of the water absorbent resin caused by vibration, it is preferable to store the water absorbent resin at a certain distance apart from a rotating machine (particularly referring to a vibratory facility, and specifically a packing machine or a classifier) in a manufacturing plant for the water absorbent resin, and specifically, the water absorbent resin is stored away at a distance of 10 m or more, more preferably 20 m or more, and still more preferably 30 m or more. Furthermore, from the viewpoint of damage and cost of the water absorbent resin caused by migration, it is preferable to use a warehouse or the like within a manufacturing plant for the water absorbent resin or in close proximity thereto (for example, within 1 km, and more preferably within 500 m), as a storage place.

(Storage Amount)

A storage amount (absolute amount) in the storage step in the present invention may be appropriately determined based on a production quantity of a manufacturing plant of the water absorbent resin and a storage period. Preferably, it is desirable to store an amount equivalent to a production quantity mentioned above (preferably 100 [kg/hr] or more, and more preferably 500 [kg/hr]) multiplied by storage days.

(Measurement of Physical Properties)

According to the present invention, physical properties measurement may be carried out by extracting a necessary amount of the water absorbent resin from each container for shipment before or after the storage step, or during the storage step, and preferably during the storage step. Furthermore, the foregoing extraction may be carried out several times by changing a time and/or a position.

At this time, a moisture content of the water absorbent resin is as described above. Furthermore, when an amount of residual monomers in the water absorbent resin is measured over time, reduction of the residual monomers can be checked. Also, various physical properties such as described below may also be measured. Meanwhile, coloration or polymer deterioration can be reduced by maintaining the storage conditions described above.

[4] Physical Properties of Polyacrylic Acid (Salt)-Based Water Absorbent Resin

A polyacrylic acid (salt)-based water absorbent resin obtainable by the present invention is preferably produced according to the method described above. That is, the polyacrylic acid (salt)-based water absorbent resin of the present invention is a water absorbent resin having an iron content of 2 ppm or less, a moisture content of 1% by weight or more, and a p-methoxyphenol content of 5 ppm to 60 ppm, and is a water absorbent resin containing at least one or more aggregating agents selected from the group consisting of polyvalent metal salts, water-insoluble fine particles and surfactants, and/or at least one or more coloration preventing agents selected from the group consisting of α-hydroxycarboxylic acid compounds, inorganic reducing agents and chelating agents. Such a water absorbent resin has less residual monomers, is less colored, and can exhibit high physical properties such as CRC, AAP and the like shown below.

Furthermore, a moisture content of the water absorbent resin of the present invention is 1% by weight or more, and preferably 3% to 20% by weight. Also, the water absorbent resin has CRC (absorption capacity without load) of preferably 25 [g/g] or more, and more preferably in the range of item (4-3). Furthermore, AAP (absorption capacity under load) is 20 [g/g] or more, and more preferably in the range of the following item (4-1). The water absorbent resin of the present invention more preferably has SFC (saline flow conductivity) of 50 [$\times 10^{-7}$ cm$^3$·s·g$^{-1}$], and preferably contains an aggregation preventing agent and/or a coloration preventing agent, and more preferably an aggregation preventing agent and a coloration preventing agent, in the range described above.

Furthermore, the water absorbent resin of the present invention may contain an iron component originating mainly from a basic substance used in neutralization. An iron content is 2 ppm in terms of Fe ion (about 2.8 ppm in terms of $Fe_2O_3$) or less, preferably 1.5 ppm or less, more preferably 1 ppm or less, and still more preferably 0.5 ppm or less. Furthermore, the lower limit of the iron content is preferably 0.001 ppm or more, and more preferably 0.01 ppm or more. Meanwhile, when neutralization is carried out by using NaOH having an iron content of 10 ppm in terms of $Fe_2O_3$, an iron content in sodium acrylate with a neutralization ratio of 75% by mole is about 3 ppm. Such a predetermined amount of iron component accelerates decomposition of the water absorbent resin when the water absorbent resin is disposed of after use. However, an excess iron component would cause deterioration or coloration of the water absorbent resin during the storage step essential in the present invention for a predetermined time or at the time of use thereafter, and therefore, it is not preferable.

Control of the iron content is mainly carried out by controlling a basic substance (particularly, caustic soda) used for neutralization, and in addition to that, can be carried out by controlling a trace amount of iron component in raw materials (acrylic acid, crosslinking agent, water and the like), and further controlling a resin coating, glass coating and stainless steel of various apparatuses and pipelines for the water absorbent resin such as the polymerization apparatus and monomer pipes used. Meanwhile, the iron content in the basic substance or the water absorbent resin can be quantified by the ICP emission spectroscopic method described in JIS K1200-6, for example, and regarding the reference material for the quantification method, reference can be made to WO 2008/090961.

In the case where a hygienic material, particularly a paper diaper is intended, it is preferable that at least one of physical properties of items (4-1) to (4-10) described below, more preferably two or more including AAP, and particularly three or more of physical properties be controlled to predetermined ranges by means of the polymerization or surface crosslinking. When physical properties described below are not satisfied, the water absorbent resin may not exhibit sufficient performance in a high concentration diaper that will be described below.

The production method of the present invention can be suitably applied to a method for producing a water absorbent resin that will be described below. Meanwhile, unless stated otherwise, physical properties described below and in Examples are defined by the EDNA method.

(4-1) Absorption Capacity Under Load (AAP)

AAP of the water absorbent resin according to the present invention is 20 [g/g] or more, preferably 22 [g/g] or more, more preferably 23 [g/g] or more, still more preferably 24 [g/g] or more, and most preferably 25 [g/g] or more. The upper limit of AAP is not particularly limited, but is preferably 30 [g/g] or less. If the AAP is less than 20 [g/g], when the water absorbent resin is used in an absorbent, there would be a risk that a water absorbent resin having less return of liquid (conventionally referred to as "Re-Wet") when a pressure is applied to the absorbent may not be obtained. The AAP can be controlled by surface crosslinking, particle size, and the like as described above.

(4-2) Liquid Permeability (SFC)

SFC of the water absorbent resin according to the present invention is preferably 30 [$\times 10^{-7}$ cm$^3$·s·g$^{-1}$] or more, more preferably 50 [$\times 10^{-7}$ cm$^3$·s·g$^{-1}$] or more, still more preferably 70 [$\times 10^{-7}$ cm$^3$·s·g$^{-1}$] or more, and particularly preferably 80 [$\times 10^{-7}$ cm$^3$·s·g$^{-1}$] or more.

If the SFC is less than 30 [$\times 10^{-7}$ cm$^3$·s·g$^{-1}$], liquid permeability would not be enhanced, and when the water absorbent resin is used in an absorbent, there would be a risk that a water absorbent resin having an excellent rate of liquid incorporation into the absorbent may not be obtained. The upper limit of SFC is not particularly limited, but the upper limit is preferably 3000 [$\times 10^{-7}$ cm$^3$·s·g$^{-1}$] or less, and more preferably 2000 [$\times 10^{-7}$ cm$^3$·s·g$^{-1}$] or less. If the SFC is larger than 3000 [$\times 10^{-7}$ cm$^3$·s·g$^{-1}$], liquid leakage from the absorbent may occur. The SFC can be controlled by means of surface crosslinking, particle size, the (2-8) (a) polyvalent metal salt, and the like as described above.

(4-3) Absorption Capacity without Load (CRC)

Absorption capacity without load (CRC) of the water absorbent resin according to the present invention is preferably 25 [g/g] or more, more preferably 27 [g/g] or more, and still more preferably 30 [g/g] or more. The upper limit of the CRC is not particularly limited, but is preferably 70 [g/g] or less, more preferably 50 [g/g] or less, and still more preferably 40 [g/g] or less.

When the CRC is adjusted to 25 [g/g] or more, in the case where the water absorbent resin is used in an absorbent such as a paper diaper, liquid (particularly, urine) can be absorbed several times. Furthermore, when the CRC is adjusted to 70 [g/g] or less, in the case where the water absorbent resin is used in an absorbent such as a paper diaper, a water absorbent resin having an excellent rate of liquid incorporation into the absorbent can be obtained. The CRC can be controlled by internal crosslinking agent, surface crosslinking agent and the like as described above.

(4-4) Water Extractable Content (Ext)

Water extractable content (Ext) of the water absorbent resin according to the present invention is preferably 35% by weight or less, more preferably 25% by weight or less, and still more preferably 15% by weight or less.

If the water extractable content is greater than 35% by weight, the water absorbent resin may have a weak gel strength and poor liquid permeability. Furthermore, when the water absorbent resin is used in an absorbent, there would be a risk that a water absorbent resin which exhibits less return of liquid (conventionally referred to as Re-Wet) when a pressure is applied to the absorbent may not be obtained. The water extractable content can be controlled by internal crosslinking agent described above or the like.

(4-5) Residual Monomers (RM)

The water absorbent resin according to the present invention preferably has less residual monomers from the viewpoint of safety, and the residual monomers are controlled to usually 500 ppm or less, preferably 400 ppm or less, and more preferably 300 ppm or less. In the present invention, the content of residual monomers in the water absorbent resin in the stage of the packaging step may be in the range described above, but the residual monomers may be reduced to the range described above, by being subjected to the storage step. Also, it is preferable to store the water absorbent resin until the amount of residual monomers is reduced by 10 ppm or more during the storage step after packaging.

(4-6) Water Absorption Rate (FSR)

A water absorption rate (FSR) of the water absorbent resin according to the present invention, as measured with 1 g of the water absorbent resin against 20 g of physiological saline, is preferably 0.1 [g/g/sec] or more, more preferably 0.15 [g/g/sec] or more, still more preferably 0.20 [g/g/sec] or more, and particularly preferably 0.25 [g/g/sec] or more. The upper limit of FSR is not particularly limited, but the upper limit is preferably 5.0 [g/g/sec] or less, and more preferably 3.0 [g/g/sec] or less. The FSR is defined by a measurement method described in WO 2009/016055.

If the FSR is less than 0.05 [g/g/sec], for example, when the water absorbent resin is used in an absorbent, liquid would not sufficiently absorbed, and there would be a risk that liquid leakage may occur. The FSR can be controlled by a particle size described above, foaming polymerization, or the like.

(4-7) Particle Size

A particle size of the water absorbent resin according to the present invention is preferably in the range described with regard to the section (2-5) pulverization step and classification step. If the particle size is out of the range described above, even in the storage period according to the present invention, there would be a risk that segregation of particles may occur, and a decrease or uneven distribution of physical properties of the water absorbent resin may be brought about.

(4-8) Moisture Content

The moisture content of the water absorbent resin according to the present invention is 1% by weight or more, preferably 3% to 20% by weight, more preferably 5% to 20% by mass, still more preferably 7% to 20% by mass, and particularly preferably 10% to 15% by mass. If the moisture content is less than 1% by weight, effects by the present invention may not be obtained, and also, a water absorbent resin having poor powder characteristics (fluidity, conveyance properties, and resistance to damage) would be obtained. In order to maintain a powder state in a predetermined packaged amount under conditions of such a moisture content, particularly a moisture content higher than a conventional one, it is preferable that the water absorbent resin contain at least one or more aggregation preventing agents selected from the group consisting of polyvalent metal salts, water-insoluble fine particles, and surfactants.

(4-9) Initial Color Tone

The water absorbent resin according to the present invention is a water absorbent resin that can be suitably used in a hygienic material such as a paper diaper, and is preferably a white powder. The water absorbent resin according to the present invention preferably exhibits L value (lightness) of at least 88 or higher, preferably 89 or higher, and more preferably 90 or higher, according to the measurement by the Hunter's Lab colorimetric system using a spectrophotometric colorimeter after the production of the water absorbent resin. Furthermore, the upper limit of L value is usually 100, but if the L value is 88, no problem occurs with the color tone in a product such as a hygienic material. Furthermore, b value is set to 0 to 12, preferably 0 to 10, and more preferably 0 to 9, and a value is set to −3 to 3, preferably −2 to 2, and more preferably −1 to 1.

The initial color tone is a color tone after the production of the water absorbent resin, but in general, the initial color tone is considered as a color tone measured before shipment from a plant. Furthermore, for example, if the water absorbent resin is stored in an atmosphere at 30° C. or lower and a relative humidity of 50% RH, the initial color tone is a value measured within one year after the production.

(4-10) Color Tone Over Time

The water absorbent resin according to the present invention is a water absorbent resin which can be suitably used in a hygienic material such as a paper diaper, and in that case, it is preferable to maintain a markedly clean white state even in a long-term storage state under conditions of high humidity or temperature.

A long-term storage state can be examined by measuring an L value (lightness) of the water absorbent resin in the Hunter's Lab colorimetric system using a spectrophotometric colorimeter, after the water absorbent resin is exposed to an atmosphere at a temperature of 70±1° C. and a relative humidity of 65±1% RH for 7 days as a long-term storage color stability acceleration test.

The water absorbent resin according to the present invention is preferably such that in the measurement of the water absorbent resin by the Hunter's Lab colorimetric system using a spectrophotometric colorimeter after the long-term storage color stability acceleration test, the water absorbent resin exhibits an L value (lightness) of at least 80 or higher, preferably 81 or higher, more preferably 82 or higher, and still more preferably 83 or higher. Meanwhile, the upper limit of the L value is usually 100, but the L value after the acceleration test of 80 or higher is a level that there are substantially no problems even in the long-term storage state under conditions of high humidity or temperature. Furthermore, a b value is set to 0 to 15, preferably 0 to 12, and more preferably 0 to 10, and an a value is set to −3 to 3, preferably −2 to 2, and more preferably −1 to 1.

[5] Packaged Product of Polyacrylic Acid (Salt)-Based Water Absorbent Resin

In the present invention, there is also provided a packaged product in which a polyacrylic acid (salt)-based water absorbent resin having an iron content in the water absorbent resin of 2 ppm or less, a moisture content of 1% by weight or more, and a p-methoxyphenol content of 5 ppm to 160 ppm, and containing at least one or more aggregation preventing agents selected from polyvalent metals, water-insoluble fine particles and a surfactants, and at least one or more coloration preventing agents selected from hydroxycarboxylic acid, inorganic or organic reducing agents and chelating agents, is packaged in a transportable container, a container bag, a paper bag, silo or the like in a unit amount of 20 kg to 10 t.

[6] Use of Polyacrylic Acid (Salt))-Based Water Absorbent Resin

The use of the water absorbent resin of the present invention is not particularly limited, but preferably, the water absorbent resin can be used in an absorbent article such as a paper diaper, a sanitary napkin, or an incontinence pad. In particular, the water absorbent resin is preferably used in a high concentration diaper (a product in which a large amount of a water absorbent resin is used in one sheet of a diaper) in which foul odor, coloration and the like originating from a raw material have hitherto caused a problem, and when the water absorbent resin is used in an upper layer part of an absorbent in an absorbent article, especially excellent performance can be exhibited.

In the case where the absorbent article contains another absorbent (pulp fibers or the like), a content (core concentration) of the water absorbent resin in the relevant absorbent article is 30% to 100% by weight, preferably 40% to 100% by weight, more preferably 50% to 100% by weight, still more preferably 60% to 100% by weight, particularly preferably 70% to 100% by weight, and most preferably 75% to 95% by weight. When the content is adjusted to within the range, effects by the present invention can be exhibited.

EXAMPLES

Hereinafter, the present invention will be more specifically described by way of Examples and Comparative Examples, but the present invention is not construed to be limited to these, and embodiments obtainable by appropriately combining the respective technical means disclosed in different Examples are also intended to be included in the scope of the present invention. Furthermore, for convenience, the unit "liter" may be indicated as "L", and the unit "% by weight" as "wt %".

Meanwhile, unless particularly stated otherwise, an electrical equipment used in Examples and Comparative Examples used a power supply of 200 V or 100 V. Furthermore, unless particularly stated otherwise, various properties of the water absorbent resin of the present invention were measured under conditions of room temperature (20° C. to 25° C.) and humidity of 50 RH %. Also, the phrase "measured quickly after sampling" means that measurement operation was initiated within 1 to 3 hours, particularly within 1 hour, after sampling of a water absorbent resin.

[Method for Measuring Physical Properties]

(a) CRC (Absorption Capacity without Load)

This was measured according to ERT441.2-02.

0.2 g (designated as weight W0 [g]) of a water absorbent resin was weighed and uniformly placed in a bag (60×60 mm) made of a non-woven fabric. The bag was heat sealed, and then the bag was immersed in 500 mL of a 0.9 wt % aqueous solution of sodium chloride regulated at 25±3° C. After 60 minutes passed, the bag was pulled up, and dehydration was carried out by using a centrifuge (centrifuge manufactured by Kokusan Co., Ltd., Model: H-122) under the conditions of 250G for 3 minutes. Thereafter, weight W1 [g] of the bag was measured.

Furthermore, the same operation was carried out without placing the water absorbent resin, and weight W2 [g] of the bag at that time was measured. CRC (absorption capacity without load) was calculated from W0 [g], W1 [g], and W2 [g] thus obtained according to the following formula.

$$CRC[g/g] = \{(W1-W2)/W0\} - 1 \quad \text{[Mathematical formula 1]}$$

(b) AAP (Absorption Capacity Under Load)

The AAP was measured according to the measurement method defined in ERT442.2-02, except that the load was changed to 4.83 kPa (0.7 psi).

(c) Ext (Extractables)

In accordance of ERT470.2-02, 1.000 g of a water absorbent resin was added to 200 ml of a 0.9 wt % aqueous solution of sodium chloride, and an amount of dissolved polymer (unit: % by weight) obtained after stirring for 16 hours was measured by pH titration.

(d) RM (Residual Monomers)

In accordance of ERT410.2-02, 1.0 of a water absorbent resin was added to 200 ml of a 0.9 wt % aqueous solution of sodium chloride, and an amount of dissolved monomers (unit: ppm) obtained after stirring for one hour at 500 rpm was measured by using HPLC (high performance liquid chromatography).

(e) PSD (Particle Size Distribution) and D50 (Weight Average Particle Size)

The PSD (particle size distribution) and D50 (weight average particle size) were measured by classifying a sample with standard sieves.

That is, 10.0 g of a water absorbent resin was placed on JIS standard sieves (The IIDA TESTING SIEVE: inner diameter 80 mm) having mesh sizes of 2000 μm, 1400 μm, 1000 μm, 850 μm, 710 μm, 600 μm, 500 μm, 425 μm, 300 μm, 212 μm, 150 μm, and 45 μm under conditions of room temperature (20° C. to 25° C.) and humidity of 50 RH %, and the water absorbent resin was classified for 5 minutes in a RO-TAP sieve shaker (manufactured by Iida Seisakusho Japan Corp.; ES 65 type sieve shaker; SER. No. 0501), prior to measurement of PSD (particle size distribution).

Furthermore, D50 (weight average particle size) means, as disclosed in U.S. Pat. No. 5,051,259, and the like, a particle size of a standard sieve corresponding to 50% by weight of all the particles. That is, a particle size distribution obtained by PSD (particle size distribution) measurement described above was used, and residual percentages (R) of various particle sizes were plotted on a logarithmic probability paper. From this graph, a particle size corresponding to R=50% by weight was read as D50 (weight average particle size).

(f) SFC (Saline Flow Conductivity)

The SFC was measured according to the method disclosed in U.S. Pat. No. 5,849,405.

(g) Initial Color Tone and Color Tone Over Time

In the present invention, color tone of a water absorbent resin was carried out with a Hunter's Lab color system. Furthermore, a spectrophotometric colorimeter, SZ-E80, manufactured by Nippon Denshoku Industries Co., Ltd. was used as a measuring apparatus (spectrophotometric colorimeter), and reflection measurement was selected as measurement conditions. Furthermore, a container for powder/paste sample (inner diameter: 30 mm, height: 12 mm), a standard round whiteboard for powder/paste No. 2, and a 30Φ translucent pipe were used.

About 5 g of a water absorbent resin was packed in the container for the powder/paste sample, and in an atmosphere at room temperature (20° C. to 25° C.) and relative humidity of 50 RH %, L value, a value, and b value on a surface of the water absorbent resin were measured.

In the present invention, color tone of a water absorbent resin immediately after production, or a water absorbent resin whose storage period in an atmosphere at air temperature of 30° C. or lower and relative humidity of 50 RH % or less was one year or less after production, was designated as "initial color tone". L value measured at this time was designated as the "lightness index before exposure".

Furthermore, the following operation was carried out as a "coloration acceleration test", and "lightness index after exposure" was measured.

The coloration acceleration test was carried out by placing a container for powder/paste sample packed with about 5 g of a water absorbent resin, in a constant temperature constant humidity chamber (small-sized environmental testing machine manufactured by Espec Corp.; Model SH-641) that had been adjusted to an atmosphere at a temperature of 70±1° C. and relative humidity of 65±1 RH %, and exposing the water absorbent resin to this high temperature high humidity atmosphere for 7 days.

Color tone for the water absorbent resin after exposure was designated as "color tone over time", and L value measured at this time was designated as "lightness index after exposure".

Meanwhile, as L value was closer to 100, a degree of whiteness increased, and as a value and b value were closer to 0 (zero), a water absorbent resin was less colored and became whiter.

(h) Moisture Content

In an aluminum cup having a diameter of bottom of about 50 mm, 1.00 g of a water absorbent resin was weighed, and a total weight W8 [g] of a sample (the water absorbent resin and the aluminum cup) was measured.

Subsequently, the sample was left to stand in an oven at atmosphere temperature of 180° C., and thus the water absorbent resin was dried. After 3 hours, the sample was taken out from the oven, and was cooled to room temperature in a desiccators. Thereafter, a total weight W9 [g] of the sample (the water absorbent resin and the aluminum cup)

after drying was measured, a the moisture content (unit: [wt %]) was calculated according to the following formula.

$$\text{Moisture content [wt \%]} = (W8-W9)/(\text{weight of water absorbent resin}) \times 100 \quad \text{[Mathematical formula 2]}$$

Meanwhile, in the case of a water absorbent resin containing polyacrylic acid ammonium salt, ammonia is liberated at a high temperature. Therefore, the measurement is carried out except that vacuum drying was carried out with atmosphere temperature changed from 180° C. to 105° C. instead.

(i) Amount of p-Methoxyphenol Contained in Water Absorbent Resin

An amount of p-methoxyphenol contained in a water absorbent resin of the present invention can be determined by analyzing a filtrate obtained by performing the same operation as in the measurement method for the (c) Ext (Extractables), except that the stirring time is changed from 16 hours to 1 hour. Specifically, when the filtrate obtained by the relevant operation is analyzed by high performance liquid chromatography, a content of p-methoxyphenol in a water absorbent resin can be determined. Meanwhile, the content of p-methoxyphenol is expressed in ppm (with respect to the water absorbent resin).

(j) Amount of Reducing Agent (Sodium Hydrogen Sulfite) Contained in Water Absorbent Resin 50 g of pure water and 0.5 g of a water absorbent resin were placed in a 200-ml beaker, and the mixture was left to stand for one hour. Subsequently, 50 g of methanol was added thereto, and then 2.5 g of a solution prepared by dissolving 2 mmol of Malachite Green in an eluent that will be described below was added thereto. This solution was stirred for about 30 minutes and then filtered, and the filtrate was analyzed by high performance liquid chromatography, to determine an amount of a reducing agent contained in the water absorbent resin. Meanwhile, the eluent is prepared by mixing 400 ml of methanol, 6 ml of n-hexane, and 100 ml of 0.01 mol/l 2-N-morpholino-ethanesulfonic acid, sodium salt. Furthermore, a calibration curve was produced by analyzing samples prepared by spiking a reducing agent into a water absorbent resin that did not contain a reducing agent.

(k) Iron Content in Aqueous Monomer Solution

An aqueous monomer solution was diluted to about 100 times with ultrapure water, and an iron content was measured by an inductively coupled plasma (ICP) emission analysis method. An iron content was measured also for ultrapure water by an inductively coupled plasma (ICP) emission analysis method, and this value was used as a blank value.

(l) Iron Content in Water Absorbent Resin 1.000 g of a water absorbent resin was weighed in a platinum crucible, and the water absorbent resin was incinerated by using an electric furnace (manufactured by Yamato Scientific Co., Ltd.; Muffle Furnace FO300). Subsequently, 5 ml of an aqueous nitric acid solution (manufactured by Wako Pure Chemical Industries, Ltd.; an aqueous solution prepared by mixing special grade nitric acid and ultrapure water at 1:1) was added to the platinum crucible taken out from the electric furnace, to dissolve the incineration product therein. Subsequently, 15 ml of ultrapure water was added thereto, to yield an aqueous solution of incineration product. Furthermore, the same operation as described above was carried out without introducing the water absorbent resin, to obtain a blank aqueous solution. The aqueous solutions obtained by the above operations were subjected to analysis by inductively coupled plasma (ICP) emission analysis method described in JIS K1200-6, to determine an iron content in the water absorbent resin.

Hereinbelow, in Examples and Comparative Examples, acrylic acid having a moisture content of 900 ppm, and as an impurity, an acetic acid content of 770 ppm and a propionic acid content of 130 μm was used, unless particularly stated otherwise. Furthermore, acrylic acid obtained in final purification step for acrylic acid was used within several hours (substantially no storage time).

Comparative Example 1

29.97 parts by weight of a 48.5 wt % aqueous solution of sodium hydroxide (containing 0.7 ppm of an iron component relative to sodium hydroxide), 35.87 parts by weight of acrylic acid (containing 70 ppm of p-methoxyphenol as a polymerization inhibitor), 0.78 part by weight of a 30 wt % aqueous solution of polyethylene glycol diacrylate (average molecular weight: 523) as an internal crosslinking agent, 0.88 part by weight of a 1 wt % aqueous solution of trisodium diethylenetriamine pentaacetate as a chelating agent, and 32.50 parts by weight of deionized water were supplied to a mixer, to prepare an aqueous monomer solution. At this time, the temperature of the aqueous monomer solution was 95° C. In the aqueous monomer solution, the amount of acetic acid was 630 ppm relative to the monomer (s), the amount of propionic acid was 110 ppm relative to the monomer(s), and the amount of iron component was 0.25 ppm relative to the monomer(s). The amount of p-methoxyphenol was 57 ppm relative to the monomer(s).

Next, 1.99 parts by weight of a 3.0 wt % aqueous solution of sodium persulfate was added as a polymerization initiator to the resultant aqueous monomer solution, and polymerization was carried out, to obtain a sheet-like water-containing gel-like crosslinked polymer (hereinafter, also referred to as "water-containing gel").

The sheet-like water-containing gel thus obtained was continuously crushed by using a meat chopper (manufactured by Hiraga Kousakusho Co., Ltd.) having a screen with a diameter of 7.5 mm, to obtain a particulate water-containing gel. At this time, the moisture content of the particulate water-containing gel was 50% by weight.

Subsequently, the particulate water-containing gel thus obtained was dried at 170° C. for 20 minutes by using a hot air circulation type dryer, to obtain a dried polymer. The dried polymer thus obtained was pulverized with a roll mill, and was further classified by using sieves having mesh sizes of 850 μm and 150 μm, to obtain a particulate water absorbent resin having a particle size of equal to or greater than 150 μm and less than 850 μm. The moisture content of the particulate water absorbent resin was 5.8% by weight, and the absorption capacity without load (CRC) was 31 [g/g].

Subsequently, an aqueous solution of surface crosslinking agent containing 0.1 part by weight of ethylene glycol diglycidyl ether (product name: DENACOL 810) and 5 parts by weight of deionized water was added to 100 parts by weight of the resultant particulate water absorbent resin, and the mixture was mixed and heat treated for 30 minutes at 120° C. Subsequently, the mixture was cooled by standing for one hour, to obtain a water absorbent resin (a1). For the water absorbent resin (a1), the amount of residual monomers and the like were measured quickly after sampling. The results are presented in the following table. Meanwhile, the absorption capacity without load (CRC) of the water absorbent resin (a1) was 27 [g/g], and the absorption capacity under load (AAP 0.7 psi) was 24 [g/g]. Furthermore, the iron content was 0.25 ppm, and the p-methoxyphenol content was 15 ppm.

Example 1

The water absorbent resin (a1) obtained in Comparative Example 1 was packaged in an amount of 25 kg per paper bag, and the packages were stored for 38 days in a warehouse in the plant premise (the travel distance from the packaging place was 50 m). The container used for the packaging was a paper bag formed from an inner plastic bag and an outer paper bag, and the paper bag can be sealed by tying the tip of the inner bag. Furthermore, the environment inside the warehouse in the storage was controlled with an air conditioner to be at an air temperature of 20° C. to 30° C. and a relative humidity of 30% to 70%.

For a water absorbent resin (A1) obtained after the passage of the storage period, the amount of residual monomers and the like were measured quickly after sampling. The results are presented in the following table. Meanwhile, the absorption capacity without load (CRC) of the water absorbent resin (A1) was 27 [g/g], and the absorption capacity under load (AAP 0.7 psi) was 24 [g/g]. Furthermore, the iron content was 0.25 ppm, and the p-methoxyphenol content was 15 ppm.

Comparative Example 2

A water absorbent resin (a2) was obtained by the same operations as in Comparative Example 1, except that the drying temperature was changed from 170° C. to 160° C. For the water absorbent resin (a2), the amount of residual monomers and the like were measured quickly after sampling. The results are presented in the following table. Furthermore, the absorption capacity without load (CRC) of the water absorbent resin (a2) was 26 [g/g], and the absorption capacity under load (AAP 0.7 psi) was 22 [g/g].

Furthermore, the moisture content of the particulate water absorbent resin before surface crosslinking was 6.8% by weight, and the absorption capacity without load (CRC) was 28 [g/g].

Example 2

The water absorbent resin (a2) obtained in Comparative Example 2 was packaged in the same manner as in Example 1 in an amount of 25 kg per paper bag, and the packages were stored for 38 days in a warehouse within the plant premise (the travel distance from the packaging place was 50 m). The environment inside the warehouse in the storage was also the same as in Example 1.

For a water absorbent resin (A2) obtained after the passage of the storage period, the amount of residual monomers and the like were measured quickly after sampling. The results are presented in the following table. Meanwhile, the absorption capacity without load (CRC) of the water absorbent resin (A2) was 26 [g/g], and the absorption capacity under load (AAP 0.7 psi) was 22 [g/g].

Comparative Example 3

29.97 parts by weight of a 48.5 wt % aqueous solution of sodium hydroxide (containing 0.7 ppm of an iron component relative to sodium hydroxide), 35.87 parts by weight of acrylic acid (containing 70 ppm of p-methoxyphenol as a polymerization inhibitor), 0.78 part by weight of a 30 wt % aqueous solution of polyethylene glycol diacrylate (average molecular weight: 523) as an internal crosslinking agent, 0.88 part by weight of a 1 wt % aqueous solution of trisodium diethylenetriamine pentaacetate as a chelating agent, and 32.50 parts by weight of deionized water were supplied to a mixer, to prepare an aqueous monomer solution. At this time, the temperature of the aqueous monomer solution first increased up to 95° C. and then decreased to 85° C. Meanwhile, the amount of acetic acid in the aqueous monomer solution was 630 ppm relative to the monomer(s), the amount of propionic acid was 110 ppm relative to the monomer(s), and the amount of iron component was 0.25 ppm relative to the monomer(s).

Subsequently, 1.99 parts by weight of a 3.0 wt % aqueous solution of sodium persulfate was added as a polymerization initiator to the resultant aqueous monomer solution, and polymerization was carried out, to obtain a sheet-like water-containing gel.

The sheet-like water-containing gel thus obtained was continuously crushed by using a meat chopper (manufactured by Hiraga Kousakusho Co., Ltd.) having a screen with a diameter of 7.5 mm, and thus a particulate water-containing gel was obtained. At this time, the moisture content of the particulate water-containing gel was 50% by weight.

Subsequently, the particulate water-containing gel thus obtained was dried at 180° C. for 40 minutes by using a hot air circulation type dryer, to obtain a dried polymer. The dried polymer thus obtained was pulverized with a roll mill, and was further classified by using sieves having mesh sizes of 850 μm and 150 μm, to obtain a particulate water absorbent resin having a particle size of equal to or greater than 150 μm and less than 850 μm. The moisture content of the resultant particulate water absorbent resin was 5.0% by weight, and the absorption capacity without load (CRC) was 34 [g/g].

Subsequently, an aqueous solution of surface crosslinking agent containing 0.3 part by weight of 1,4-butanediol, 3 parts by weight of deionized water and 0.01 part by weight of polyoxyethylene sorbitan monostearate as a surfactant was added to 100 parts by weight of the resultant particulate water absorbent resin, and the mixture was mixed and heat treated for 30 minutes at 200° C. Subsequently, the mixture was cooled by standing for one hour, to obtain a water absorbent resin (a3). For the water absorbent resin (a3), the amount of residual monomers and the like were measured quickly after sampling. The results are presented in the following table. Meanwhile, the absorption capacity without load (CRC) of the water absorbent resin (a3) was 28 [g/g], and the absorption capacity under load (AAP 0.7 psi) was 24 [g/g]. Furthermore, the iron content was 0.25 ppm, and the p-methoxyphenol content was 12 ppm.

Comparative Example 4

The water absorbent resin (a3) obtained in Comparative Example 3 was packaged in an amount of 20 kg per container in a hard polyethylene container (holding 20 kg) having a capacity of 30 L, and the packages were stored for 90 days in a warehouse within the same plant premise as that used in Example 1. The container used for packaging was a hard polyethylene container and could be sealed with a lid. Furthermore, the environment inside the warehouse in the storage was controlled to be at an air temperature of 20° C. to 30° C. and a relative humidity of 30% to 60%.

For a water absorbent resin (a4) obtained after the passage of the storage period, the amount of residual monomers and the like were measured quickly after sampling. The results are presented in the following table. Meanwhile, the absorption capacity without load (CRC) of the water absorbent resin (a4) was 28 [g/g], and the absorption capacity under load (AAP 0.7 psi) was 24 [g/g]. Furthermore, the iron content was 0.25 ppm.

Comparative Example 5

While the water absorbent resin (a3) thus obtained in Comparative Example 3 was stirred, 0.1 part by weight of silicon dioxide (product name: AEROSIL 200) was added thereto as inorganic fine particles, and an aqueous liquid formed from 10 parts by weight of deionized water and 1 part by weight of propylene glycol as a mixing aid was added thereto to adjust a moisture content. The mixture was left to stand for one hour, to obtain a water absorbent resin (a5). For the water absorbent resin (a5), the amount of residual monomers and the like were measured quickly after sampling. The results are presented in the following table. Meanwhile, the absorption capacity without load (CRC) of the water absorbent resin (a5) was 26 [g/g], and the absorption capacity under load (AAP 0.7 psi) was 23 [g/g]. Furthermore, the iron content was 0.23 ppm.

Comparative Example 6

The water absorbent resin (a5) obtained in Comparative Example 5 was packaged in an amount of 20 kg per container in the hard polyethylene container used in Comparative Example 4, and the packages were stored for one day in a warehouse in the same plant premise as that used in Example 1. The container used for packaging was a hard polyethylene container and could be sealed with a lid. Furthermore, the environment inside the warehouse in the storage was controlled to be at an air temperature of 20° C. to 30° C. and a relative humidity of 30% to 60%.

For a water absorbent resin (a6) obtained after the passage of the storage period, the amount of residual monomers and the like were measured quickly after sampling. The results are presented in the following table. Meanwhile, the absorption capacity without load (CRC) of the water absorbent resin (a6) was 26 [g/g], and the absorption capacity under load (AAP 0.7 psi) was 23 [g/g]. Furthermore, the iron content was 0.23 ppm.

Examples 3 to 6

Water absorbent resins (A3 to A6) were obtained by the same operations as in Comparative Example 6, except that the period for storage in the warehouse was changed to 3 days (Example 3), 9 days (Example 4), 13 days (Example 5), and 85 days (Example 6)

For water absorbent resins (A3 to A6) obtained after the passage of the storage periods, the amount of residual monomers and the like were measured quickly after sampling. The results are presented in the following table. Meanwhile, the absorption capacity without load (CRC) of the water absorbent resins (A3 to A6) was 26 [g/g] in all cases. The p-methoxyphenol content of the water absorbent resins (A3 to A6) was 10 ppm.

Comparative Example 7

A water absorbent resin (a7) was obtained by the same operations as in Comparative Example 6, except that the period for storage in the warehouse was changed to 125 days.

For the water absorbent resin (a7) obtained after the passage of the storage period, the amount of residual monomers and the like were measured quickly after sampling. The results are presented in the following table. Meanwhile, it was observed that a portion of the water absorbent resin (a7) aggregated, and fluidity was decreased. Furthermore, the water absorbent resin turned yellow as compared with the water absorbent resins (A3 to A6).

Comparative Example 8

A water absorbent resin (a8) was obtained by the same operations as in Comparative Example 5, except that 0.02 parts by weight of sodium hydrogen sulfite as a reducing agent was further added to the aqueous liquid formed from deionized water and propylene glycol. For the water absorbent resin (a8), the amount of residual monomers and the like were measured quickly after sampling. The results are presented in the following table.

Comparative Example 9

The water absorbent resin (a8) obtained in Comparative Example 8 was packaged in an amount of 20 kg per container in the hard polyethylene container used in Comparative Example 4, and the packages were stored for one day in a warehouse in the same plant premise as that used in Example 1. The container used for packaging was a hard polyethylene container and could be sealed with a lid. Furthermore, the environment inside the warehouse in the storage was controlled to be at an air temperature of 20° C. to 30° C. and a relative humidity of 30% to 60%.

For a water absorbent resin (a9) obtained after the passage of the storage period, the amount of residual monomers and the like were measured quickly after sampling. The results are presented in the following table. Meanwhile, the p-methoxyphenol content of the water absorbent resin (a9) was 7 ppm.

Examples 7 to 9

Water absorbent resins (A7 to A9) were obtained by the same operations as in Comparative Example 8, except that the period for storage in the warehouse was changed to 3 days (Example 7), 6 days (Example 8), and 13 days (Example 9), and thus.

For the water absorbent resins (A7 to A9) obtained after the passage of the storage periods, the amount of residual monomers and the like were measured quickly after sampling. The results are presented in the following table.

Comparative Example 10

46 parts by weight of 28 wt % aqueous ammonia (containing 0.1 ppm of an iron component), 49 parts by weight of a 48.5 wt % aqueous solution of sodium hydroxide (containing 0.7 ppm of an iron component relative to sodium hydroxide), 144 parts by weight of acrylic acid (containing 70 ppm of p-methoxyphenol as a polymerization inhibitor), 1.0 part by weight of a 10 wt % aqueous solution of polyethylene glycol diacrylate (average molecular weight: 523) as an internal crosslinking agent, 3.4 parts by weight of a 1 wt % aqueous solution of trisodium diethylenetriamine pentaacetate as a chelating agent, and 32 parts by weight of deionized water were supplied to a mixer, to prepare an aqueous monomer solution. At this time, the temperature of the aqueous monomer solution was 95° C. In the aqueous monomer solution, the amount of iron component was 0.15 ppm relative to the monomer(s), the amount of acetic acid was 650 ppm relative to the monomer(s), and the amount of propionic acid was 110 ppm relative to the monomer(s).

Subsequently, 6 parts by weight of a 1.0 wt % aqueous solution of 2,2'-azobis(2-amidinopropane)dihydrochloride as a polymerization initiator was added to the resultant aqueous monomer solution, and polymerization was carried out, to obtain a sheet-like water-containing gel.

The sheet-like water-containing gel thus obtained was continuously crushed by using a meat chopper (manufactured by Hiraga Kousakusho Co., Ltd.) having a screen with a diameter of 7.5 mm, to obtain a particulate water-containing gel. At this time, the moisture content of the particulate water-containing gel was 32% by weight.

Subsequently, the particulate water-containing gel thus obtained was dried at 170° C. for 20 minutes by using a hot air circulation type dryer, to obtain a dried polymer. The dried polymer thus obtained was pulverized with a roll mill, and was further classified by using sieves having mesh sizes of 850 μm and 150 μm, to obtain a particulate water absorbent resin having a particle size of equal to or greater than 150 μm and less than 850 μm. The moisture content of this particulate water absorbent resin was 6.2% by weight, and the absorption capacity without load (CRC) was 40 [g/g].

Subsequently, an aqueous solution of surface crosslinking agent containing 0.1 part by weight of ethylene glycol diglycidyl ether (product name: DENACOL EX810) and 5 parts by weight of deionized water was added to 100 parts by weight of the resultant particulate water absorbent resin, and the mixture was mixed and heat treated for 30 minutes at 120° C. Subsequently, the mixture was cooled by standing for one hour, to obtain a water absorbent resin (a10). For the water absorbent resin (a10), the amount of residual monomers and the like were measured quickly after sampling. The results are presented in the following table. Meanwhile, the iron content of the water absorbent resin (a10) was 0.15 ppm, and the p-methoxyphenol content was 15 ppm.

Example 10

The water absorbent resin (a10) obtained in Comparative Example 10 was packaged in an amount of 20 kg per container in the hard polyethylene container used in Comparative Example 4, and the packages were stored for 35 days in a warehouse in the same plant premise as that used in Example 1. The container used for packaging was a hard polyethylene container and could be sealed with a lid. Furthermore, the environment inside the warehouse at the time of storage was controlled to be at an air temperature of 20° C. to 30° C. and a relative humidity of 30% to 60%.

For a water absorbent resin (A10) obtained after the passage of the storage period, the amount of residual monomers and the like were measured quickly after sampling. The results are presented in the following table.

Comparative Example 11

100 parts by weight of 28 wt % aqueous ammonia (containing 0.1 ppm of an iron component), 216 parts by weight of acrylic acid (containing 70 ppm of p-methoxyphenol as a polymerization inhibitor), 1.57 parts by weight of a 10 wt % aqueous solution of polyethylene glycol diacrylate (average molecular weight: 523) as an internal crosslinking agent, 4.93 parts by weight of a 1 wt % aqueous solution of trisodium diethylenetriamine pentaacetate as a chelating agent, and 79 parts by weight of deionized water were supplied to a mixer, to prepare an aqueous monomer solution. At this time, the temperature of the aqueous monomer solution was 95° C. In the aqueous monomer solution, the amount of iron component was 0.05 ppm relative to the monomer(s), the amount of acetic acid was 680 ppm relative to the monomer(s), and the amount of propionic acid was 120 ppm relative to the monomer(s).

Subsequently, 9 parts by weight of a 1.0 wt % aqueous solution of 2,2'-azobis(2-amidinopropane)dihydrochloride as a polymerization initiator was added to the resultant aqueous monomer solution, and polymerization was carried out, to obtain a sheet-like water-containing gel.

The sheet-like water-containing gel thus obtained was continuously crushed by using a meat chopper (manufactured by Hiraga Kousakusho Co., Ltd.) having a screen with a diameter of 7.5 mm, to obtain a particulate water-containing gel. At this time, the moisture content of the particulate water-containing gel was 30% by weight.

Subsequently, the particulate water-containing gel thus obtained was dried at 170° C. for 20 minutes by using a hot air circulation type dryer, to obtain a dried polymer. The dried polymer thus obtained was pulverized with a roll mill, and was further classified by using sieves having mesh sizes of 850 μm and 150 μm, to obtain a particulate water absorbent resin having a particle size of equal to or greater than 150 μm and less than 850 μm. The moisture content of the resultant particulate water absorbent resin was 6.0% by weight, and the absorption capacity without load (CRC) was 32 [g/g].

Subsequently, an aqueous solution of surface crosslinking agent containing 0.1 part by weight of ethylene glycol diglycidyl ether (product name: DENACOL EX810) and 5 parts by weight of deionized water was added to 100 parts by weight of the resultant particulate water absorbent resin, and the mixture was mixed and heat treated for 30 minutes at 120° C. Subsequently, the mixture was cooled by standing for one hour, to obtain a water absorbent resin (a11). For the water absorbent resin (a11), the amount of residual monomers and the like were measured quickly after sampling. The results are presented in the following table. Meanwhile, the iron content of the water absorbent resin (a11) was 0.05 ppm, and the p-methoxyphenol content was 17 ppm.

Comparative Example 12

The water absorbent resin (a11) obtained in Comparative Example 11 was packaged in an amount of 20 kg per container in the hard polyethylene container used in Comparative Example 4, and the packages were stored for one day in a warehouse in the same plant premise as that used in Example 1. The container used for packaging was a hard polyethylene container and could be sealed with a lid. Furthermore, the environment inside the warehouse in the storage was controlled to be at an air temperature of 20° C. to 30° C. and a relative humidity of 30% to 60%.

For a water absorbent resin (a12) obtained after the passage of the storage period, the amount of residual monomers and the like were measured quickly after sampling. The results are presented in the following table.

Examples 11 to 14

Water absorbent resins (A11 to A14) were obtained by the same operations as in Comparative Example 12, except that the period for storage in the warehouse was changed to 3 days (Example 11), 7 days (Example 12), 14 days (Example 13), and 79 days (Example 14).

For the water absorbent resins (A11 to A14) obtained after the passage of the storage periods, the amount of residual monomers and the like were measured quickly after sampling. The results are presented in the following table.

Comparative Example 13

A water absorbent resin (a13) was obtained by the same operations as in Comparative Example 12, except that the period for storage in the warehouse was changed to 120 days.

For the water absorbent resin (a13) obtained after the passage of the storage period, the amount of residual monomers and the like were measured quickly after sampling. The results are presented in the following table. Meanwhile, it was observed that a portion of the water absorbent resin (a13) aggregated, and fluidity was decreased.

Example 15

A water absorbent resin (A15) was obtained by the same operations as in Example 14, except that the period for storage in the warehouse was extended by one day to be 80 days. At this time, the temperature inside the warehouse during the extended storage period temporarily increased up to 40° C.

For the water absorbent resin (A15) obtained after the passage of the storage period, the amount of residual monomers and the like were measured quickly after sampling. The results are presented in the following table. Meanwhile, it was observed that a portion of the water absorbent resin (A15) aggregated, and fluidity was decreased.

Example 16

A water absorbent resin (A16) was obtained by the same operations as in Example 15, except that 0.1 part by weight of silicon dioxide (product name: AEROSIL 200) as inorganic fine particles was added and mixed after the surface crosslinking step.

For the water absorbent resin (A16) obtained after the passage of the storage period, the amount of residual monomers and the like were measured quickly after sampling. The results are presented in the following table. Meanwhile, although the temperature inside the warehouse temporarily reached 40° C. during the storage period, aggregation of the water absorbent resin (A16) was not observed.

Comparative Example 14

A water absorbent resin (a14) was obtained by the same operations as in Example 5, except that an aqueous solution of sodium hydroxide containing 8 ppm of an iron component was used in place of the aqueous solution of sodium hydroxide containing 0.7 ppm (relative to sodium hydroxide) of an iron component. Meanwhile, the amount of iron component in the aqueous monomer solution was 2.3 ppm relative to the monomer(s).

For the water absorbent resin (a14) obtained after the passage of the storage period, the amount of residual monomers and the like were measured quickly after sampling. The results are presented in the following table. Meanwhile, in the water absorbent resin (a14), yellowing was recognized by visual inspection as compared with the water absorbent resin (A5).

Example 17

A water absorbent resin (A17) was obtained by the same operations as in Example 1, except that each of acetic acid and propionic acid were added to the raw material acrylic acid so as to give an amount of 1000 ppm. Meanwhile, the addition of the acetic acid and propionic acid was intended for assumption of acrylic acid obtained by a different purification method.

For the water absorbent resin (A17) obtained after the passage of the storage period, the packaging container was opened at the time of sampling, and unpleasant odor (acid odor) was detected. Furthermore, the amount of residual monomers and the like were measured quickly after sampling. The results are presented in the following table.

Comparative Example 15

A water absorbent resin (a15) was obtained by the same operations as in Comparative Example 1, except that acrylic acid having a p-methoxyphenol content of 200 ppm was used in place of acrylic acid having a p-methoxyphenol content of 70 ppm. Meanwhile, the amount of p-methoxyphenol in the aqueous monomer solution was 164 ppm relative to the monomer(s), and although the polymerization time was slightly delayed in the polymerization step, polymerization was carried out without any problem.

For the water absorbent resin (a15), the amount of residual monomers and the like were measured quickly after sampling. The results are presented in the following table. Meanwhile, the water absorbent resin (a15) was colored light brown, and the degree of whiteness was poor. Furthermore, the iron content of the water absorbent resin (a15) was 0.25 ppm, and the p-methoxyphenol content was 65 ppm.

Example 18

The water absorbent resin (a15) obtained in Comparative Example 15 was packaged in an amount of 25 kg per paper bag in the same manner as in Example 1, and the packages were stored for 38 days in a warehouse within the plant premise (the travel distance from the packaging place was 50 m). Meanwhile, the environment inside the warehouse in the storage was also the same as that in Example 1.

For a water absorbent resin (A18) obtained after the passage of the storage period, the amount of residual monomers and the like were measured quickly after sampling. The results are presented in the following table.

Example 19

The same operations as in Example 1 were carried out, except that a paper bag which did not have a vinyl inner bag was used as the container for packaging, and the packages were stored for 38 days in a warehouse within the plant premise (the travel distance from the packaging place was 50 m). Meanwhile, the environment inside the warehouse at the time of storage was the same as that in Example 1.

For a water absorbent resin (A19) obtained after the passage of the storage period, the amount of residual monomers and the like were measured quickly after sampling. The results are presented in the following table. Meanwhile, in the water absorbent resin (A19), a tendency of deterioration of fluidity was confirmed.

Example 20

The same operations as in Example 1 were carried out, except that the storage place for the water absorbent resin was changed to a warehouse located at a travel distance of 100 km from the packaging place (transported by a truck), and the packages were stored for 38 days in that warehouse. Meanwhile, the environment inside the warehouse at the time of storage was the same as that in Example 1.

For a water absorbent resin (A20) obtained after the passage of the storage period, the amount of residual monomers and the like were measured quickly after sampling. The results are presented in the following table. Meanwhile, it was observed that in the water absorbent resin (A20), severe segregation occurred, and the water absorbent resin fine powder aggregated in the vicinity of the bottom of the packaging containers.

Comparative Example 16

27.24 parts by weight of a 48.5 wt % aqueous solution of sodium hydroxide (containing 0.7 ppm of an iron component relative to sodium hydroxide), 31.74 parts by weight of acrylic acid (containing 70 ppm of p-methoxyphenol as a polymerization inhibitor), 1.61 parts by weight of a 10 wt % aqueous solution of polyethylene glycol diacrylate (average molecular weight: 523) as an internal crosslinking agent, and 38.54 parts by weight of deionized water were supplied to a mixer, to prepare an aqueous monomer solution, and the resultant aqueous monomer solution was cooled. At this time, the temperature of the aqueous monomer solution was 30° C. Meanwhile, in the aqueous monomer solution, the amount of acetic acid was 630 ppm relative to the monomer(s), the amount of propionic acid was 110 ppm relative to the monomer(s), and the amount of iron component was 0.25 ppm relative to the monomer(s). The amount of p-methoxyphenol was found by calculation to be 57 ppm relative to the monomer(s).

In a kneader equipped with two sigma-shaped blades, the aqueous monomer solution was introduced, and nitrogen gas was blown into the aqueous monomer solution, to reduce dissolved oxygen in the aqueous monomer solution, and at the same time, to replace the entirety of the interior of the kneader with nitrogen. Subsequently, while the blades of the kneader were rotated, cold water at 10° C. was circulated through the jacket, so as to adjust the temperature of the aqueous monomer solution to 20° C.

Subsequently, 0.734 part by weight of a 3 wt % aqueous solution of sodium persulfate as a polymerization initiator, and 0.132 part by weight of 1 wt % L-ascorbic acid were added to the aqueous monomer solution, and polymerization was initiated. The system was further stirred for 30 minutes, and was aged, to obtain as a polymerization product a water-containing gel-like polymer having a weight average particle size (D50) of about 2.0 mm.

Subsequently, the water-containing gel-like polymer thus obtained was dried at 170° C. for 20 minutes by using a hot air circulation type dryer, to obtain a dried polymer. The dried polymer thus obtained was pulverized with a roll mill, and was further classified by using sieves having mesh sizes of 850 μm and 180 μm, to obtain a particulate water absorbent resin having a particle size of equal to or greater than 180 μm and less than 850 μm. The moisture content of the resultant particulate water absorbent resin was 5.1% by weight, and the absorption capacity without load (CRC) was 33 [g/g].

Subsequently, an aqueous solution of surface crosslinking agent containing 0.1 part by weight of ethylene glycol diglycidyl ether (product name: DENACOL 810) and 5 parts by weight of deionized water was added to 100 parts by weight of the resultant particulate water absorbent resin, and the mixture was mixed and heat treated for 30 minutes at 120° C. Subsequently, the mixture was cooled by standing for one hour, to obtain a water absorbent resin (a16). For the water absorbent resin (a16), the amount of residual monomers and the like were measured quickly after sampling. The results are presented in the following table. Meanwhile, the absorption capacity without load (CRC) of the water absorbent resin (a16) was 28 [g/g], and the absorption capacity under load (AAP 0.7 psi) thereof was 23 [g/g]. Furthermore, the iron content was 0.25 ppm, and the p-methoxyphenol content was 13 ppm.

Example 21

The water absorbent resin (a16) obtained in Comparative Example 16 was packaged in an amount of 20 kg per container in a hard polyethylene container in the same manner as in Example 6, and the packages were stored for 85 days in a warehouse within the plant premise (the travel distance from the packaging place was 50 m). Furthermore, the environment inside the warehouse in the storage was also the same as that in Example 6.

For a water absorbent resin (A21) obtained after the passage of the storage period, the amount of residual monomers and the like were measured quickly after sampling. The results are presented in the following table. It was confirmed that the resultant water absorbent resin (A21) turned yellow during the storage.

Examples 22 to 24

Water absorbent resins (A22) to (A24) were obtained by the same operations as in Example 1, except that acrylic acid which was obtained by storing acrylic acid obtained in the final purification step for acrylic acid for 30 days (Example 22), 10 days (Example 23), and one day (Example 24) was used as a raw material acid for the water absorbent resin.

The residual monomers in the water absorbent resins (A22) to (A24) thus obtained were measured, to be confirmed that the amount of residual monomers increased by about 20 ppm per day during the storage of acrylic acid.

Examples 25 to 27

Water absorbent resins (A25) to (A27) were obtained by the same operations as in Examples 22 to 24, except that instead of acrylic acid (100 wt %), a 80 wt % aqueous solution of acrylic acid was used. Meanwhile, the acrylic acid was stored in a state of a 80 wt % aqueous solution of acrylic acid.

The residual monomers in the water absorbent resins (A25) to (A27) thus obtained were measured, to be confirmed that the amount of residual monomers increased by about 50 ppm per day during the storage of the aqueous solution of acrylic acid.

Example 28

A water absorbent resin (A28) was obtained by the same operations as in Example 5, except that an aqueous liquid formed from 18 parts by weight of deionized water and 1 part by weight of propylene glycol as a mixing aid was used in place of the aqueous liquid formed from 10 parts by weight of deionized water and 1 part by weight of propylene glycol as a mixing aid. The absorption capacity without load (CRC) of the water absorbent resin (A28) thus obtained was 24 [g/g], and the absorption capacity under load (AAP 0.7 psi) was 21 [g/g]. Furthermore, the amount of residual monomers was 268 ppm, and the moisture content was 21% by weight.

TABLE 1

| | Water absorbent resin | After standing for 1 hour | | | Storage step Storage period | After passage of storage period | | | Change in moisture content (2) − (1) | Change in residual monomers ②−① | Measured value | Corrected value relative to solid content (1 − ②/①) × 100 |
|---|---|---|---|---|---|---|---|---|---|---|---|---|
| | | Residual monomers ① | | | | Residual monomers ② | | | | | | |
| | | Moisture content (1) | Measured value | Corrected value relative to solid content | | Moisture content (2) | Measured value | Corrected value relative to solid content | | | | |
| | | [wt %] | [ppm] | [ppm] | [day(s)] | [wt %] | [ppm] | [ppm] | [wt %] | [ppm] | [%] | [%] |
| Comp. Ex. 1 | a1 | 6.1 | 704 | 750 | 0 | — | — | — | — | — | — | — |
| Example 1 | A1 | ↑ | ↑ | ↑ | 38 | 7.7 | 680 | 737 | 1.6 | 24.0 | 3.4 | 1.7 |
| Comp. Ex. 2 | a2 | 7.3 | 541 | 584 | 0 | — | — | — | — | — | — | — |
| Example 2 | A2 | ↑ | ↑ | ↑ | 38 | 8.6 | 529 | 579 | 1.3 | 12.0 | 2.2 | 0.8 |
| Comp. Ex. 3 | a3 | 0.8 | 341 | 344 | 0 | — | — | — | — | — | — | — |
| Comp. Ex. 4 | a4 | ↑ | ↑ | ↑ | 90 | 1.3 | 339 | 343 | 0.5 | 2.0 | 0.6 | 0.1 |
| Comp. Ex. 5 | a5 | 12.8 | 307 | 352 | 0 | — | — | 352 | — | — | — | — |
| Comp. Ex. 6 | a6 | ↑ | ↑ | ↑ | 1 | 12.8 | 305 | 350 | 0 | 2.0 | 0.7 | 0.7 |
| Example 3 | A3 | ↑ | ↑ | ↑ | 3 | 12.8 | 303 | 347 | 0 | 4.0 | 1.3 | 1.3 |
| Example 4 | A4 | ↑ | ↑ | ↑ | 9 | 12.9 | 302 | 347 | 0.1 | 5.0 | 1.6 | 1.5 |
| Example 5 | A5 | ↑ | ↑ | ↑ | 13 | 13.2 | 300 | 346 | 0.4 | 7.0 | 2.3 | 1.8 |
| Example 6 | A6 | ↑ | ↑ | ↑ | 85 | 14.1 | 298 | 347 | 1.3 | 9.0 | 2.9 | 1.5 |
| Comp. Ex. 7 | a7 | ↑ | ↑ | ↑ | 125 | 15.0 | 294 | 346 | 2.2 | 13.0 | 4.2 | 1.8 |
| Comp. Ex. 8 | a8 | 13.2 | 201 | 232 | 0 | — | — | 232 | — | — | — | — |
| Comp. Ex. 9 | a9 | ↑ | ↑ | ↑ | 1 | 13.2 | 194 | 224 | 0 | 7.0 | 3.5 | 3.5 |
| Example 7 | A7 | ↑ | ↑ | ↑ | 3 | 13.3 | 185 | 213 | 0.1 | 16.0 | 8.0 | 7.9 |
| Example 8 | A8 | ↑ | ↑ | ↑ | 6 | 13.3 | 183 | 211 | 0.1 | 18.0 | 9.0 | 8.9 |
| Example 9 | A9 | ↑ | ↑ | ↑ | 13 | 13.4 | 183 | 211 | 0.2 | 18.0 | 9.0 | 8.7 |

TABLE 2

| | Water absorbent resin | After standing for 1 hour | | | Storage step Storage period | After passage of storage period | | | Change in moisture content (2) − (1) | Change in residual monomers ②−① | Measured value | Corrected value relative to solid content (1 − ②/①) × 100 |
|---|---|---|---|---|---|---|---|---|---|---|---|---|
| | | Residual monomers ① | | | | Residual monomers ② | | | | | | |
| | | Moisture content (1) | Measured value | Corrected value relative to solid content | | Moisture content (2) | Measured value | Corrected value relative to solid content | | | | |
| | | [wt %] | [ppm] | [ppm] | [day(s)] | [wt %] | [ppm] | [ppm] | [wt %] | [ppm] | [%] | [%] |
| Comp. Ex. 10 | a10 | 4.3 | 106 | 111 | 0 | — | — | — | — | — | — | — |
| Example 10 | A10 | ↑ | ↑ | ↑ | 35 | 5.5 | 89 | 94 | 1.2 | 17.0 | 16.0 | 15.0 |
| Comp. Ex. 11 | a11 | 5.1 | 165 | 174 | 0 | — | 165 | — | — | — | — | — |
| Comp. Ex. 12 | a12 | ↑ | ↑ | ↑ | 1 | — | 161 | — | — | 4.0 | 2.4 | — |
| Example 11 | A11 | ↑ | ↑ | ↑ | 3 | — | 152 | — | — | 13.0 | 7.9 | — |
| Example 12 | A12 | ↑ | ↑ | ↑ | 7 | 5.5 | 151 | 160 | 0.4 | 14.0 | 8.5 | 8.1 |
| Example 13 | A13 | ↑ | ↑ | ↑ | 14 | 6.2 | 151 | 161 | 1.1 | 14.0 | 8.5 | 7.4 |
| Example 14 | A14 | ↑ | ↑ | ↑ | 79 | 6.5 | 149 | 159 | 1.4 | 16.0 | 9.7 | 8.3 |
| Comp. Ex. 13 | a13 | ↑ | ↑ | ↑ | 120 | 6.7 | 149 | 160 | 1.6 | 16.0 | 9.7 | 8.1 |

TABLE 3

| | Water absorbent resin | After standing for 1 hour | | | | After passage of storage period | | | | Change in residual monomers | | |
|---|---|---|---|---|---|---|---|---|---|---|---|---|
| | | Residual monomers ① | | | | Residual monomers ② | | | | | | Corrected |
| | | Moisture content (1) | Measured value | Corrected value relative to solid content | Storage step Storage period | Moisture content (2) | Measured value | Corrected value relative to solid content | Change in moisture content (2) − (1) | ② − ① | Measured value (1 − ②/①) | value relative to solid content (1 − ②/①) × 100 |
| | resin | [wt %] | [ppm] | [ppm] | [day(s)] | [wt %] | [ppm] | [ppm] | [wt %] | [ppm] | [%] | [%] |
| Example 15 | A15 | 5.1 | 165 | 174 | 80 | 6.5 | 137 | 147 | 1.4 | 28.0 | 17.0 | 15.7 |
| Example 16 | A16 | 5.1 | 165 | 174 | 80 | 6.4 | 139 | 149 | 1.3 | 26.0 | 15.8 | 14.6 |
| Comp. Ex. 14 | a14 | 13.5 | 431 | 498 | 13 | 15.1 | 411 | 484 | 1.6 | 20.0 | 4.6 | 2.8 |
| Example 17 | A17 | 6.4 | 623 | 666 | 38 | 7.7 | 601 | 651 | 1.3 | 22.0 | 3.5 | 2.2 |
| Comp. Ex. 15 | a15 | 6.3 | 857 | 915 | 0 | — | — | — | — | — | — | — |
| Example 18 | A18 | ↑ | ↑ | ↑ | 38 | 8.0 | 827 | 899 | 1.7 | 30.0 | 3.5 | 1.7 |
| Example 19 | A19 | 6.1 | 704 | 750 | 38 | 8.3 | 654 | 713 | 2.2 | 50.0 | 7.1 | 4.9 |
| Example 20 | A20 | 6.1 | 704 | 750 | 38 | 7.8 | 666 | 722 | 1.7 | 38.0 | 5.4 | 3.7 |
| Comp. Ex. 16 | a16 | 6.8 | 599 | 643 | 0 | — | — | — | — | — | — | — |
| Example 21 | A21 | ↑ | ↑ | ↑ | 85 | 8.2 | 580 | 632 | 1.4 | 19.0 | 3.2 | 1.7 |

CONCLUSIONS

In Example 1 and Example 2, the moisture content increased by 1.6% by weight (Example 1) and 1.3% by weight (Example 2), respectively, while the residual monomers had further decreased, even after the influence of increase in the moisture content was excluded by calculating the amount of residual monomers in terms of the solid content.

In Example 1 and Example 2, the moisture content increased by 1.6% by weight (Example 1) and 1.3% by weight (Example 2), respectively, and the amount of residual monomers decreased by 24 ppm (Example 1) and 12 ppm (Example 2), respectively. In regard to the residual monomers, even the corrected values based on the solid content in which the influence of the increase in the moisture content was excluded, also decreased. That is, it was confirmed that the residual monomers decreased by the storage for 38 days.

In Examples 3 to 6 and Comparative Examples 5 to 7, the water absorbent resin having a moisture content of 12.8% by weight was stored for 0 days to 125 days. In the storage for 0 days to less than 3 days, the residual monomers tended to decrease, but the values were not stabilized, while after 3 days, the amount of residual monomers were stabilized in a reduced state. On the other hand, in the storage for 125 days in Comparative Example 7, the increment in the moisture content was 2% by weight or more, aggregation occurred in a portion of the water absorbent resin, and coloration was also observed.

In Examples 7 to 9 and Comparative Examples 8 and 9, sodium hydrogen sulfite was added to the water absorbent resin having a moisture content of 13.2% by weight, and the water absorbent resin was stored for 0 to 13 days. In the storage for 0 days to less than 3 days, the residual monomers tended to decrease, but the values were not stabilized, while after 3 days, the amounts of residual monomers were stabilized in a reduced state. Furthermore, in Comparative Examples 5 and 6 and Examples 3 to 5 in which no sodium hydrogen sulfite was added, the absolute amount of residual monomers and the decrement thereof increased.

In Examples 10 to 14 and Comparative Examples 10 to 13, by using ammonium acrylate in an amount of 40% by mole or 55% by mole relative to the total amount of monomer(s), in the storage for 0 days to less than 3 days, the residual monomers tend to decrease, but the value was not stabilized, while after 3 days, the amount of residual monomers was stabilized in a reduced state. Furthermore, in Comparative Examples 5 to 6 and Examples 3 to 5 wherein the same operations except for the polymerization step were carried out, the absolute amount of residual monomers and the decrement thereof increased.

From the results of Example 15 and Example 16, it was confirmed that aggregation can be prevented by the addition of inorganic fine particles.

In Comparative Example 14, a large amount of iron component induced deterioration of color tone of the water absorbent resin during the storage.

In Example 17, a large total content of acetic acid and propionic acid as of 2000 ppm (relative to the monomer(s)) induced saturation of foul odor in the container during the storage, and when the containers were opened, unpleasant odors were detected.

From the results of Comparative Example 15 and Example 18, it was confirmed that a large amount of p-methoxyphenol induced deterioration of color tone of the water absorbent resin.

In Example 19, it is speculated that since a paper bag which lacked a vinyl inner bag was used, the water absorbent resin absorbed moisture in the atmosphere during the long-term storage, and to induce decrease in fluidity of the water absorbent resin.

In Example 20, it is speculated that as the water absorbent resin was transported over a long distance by a truck, the water absorbent resin inside the paper bag was segregated. Furthermore, the segregated fine powder tended to produce aggregates easily during the long term storage.

Comparative Example 16 and Example 21 are an example in which α-hydroxycarboxylic acid, a reducing agent, or a chelating agent was not used as a coloration preventing agent. Physical properties of the water absorbent resins obtained in the Example and Comparative Example were almost equivalent to those of Example 6, but it was confirmed that color tone was deteriorated during the long-term storage.

It was noted from Examples 22 to 24 and Examples 25 to 27 that further reduction of residual monomers can be attained by shortening a storage period of acrylic acid or an aqueous solution of acrylic acid. That is, it is preferable to connect (connected via a pipeline, particularly connected over the distance described above) the production process for acrylic acid (particularly, a final purification step involving distillation or crystallization) and the production process for the water absorbent resin. Furthermore, it is noted that it is preferable to connect the production process for acrylic acid as 100% acrylic acid but not in an aqueous solution state with the production process for the water absorbent resin.

Since in Example 28, a moisture content was high, CRC and AAP decreased, suggesting a risk of aggregation.

As mentioned above, it was confirmed that residual monomers could be decreased during the storage step according to the present invention. Furthermore, in regard to deterioration of fluidity or color tone that may occur in the storage step, it is preferable to employ predetermined storage conditions, and to use an aggregation preventing agent or a coloration preventing agent.

INDUSTRIAL APPLICABILITY

The water absorbent resin obtained by the production method of the present invention can be advantageously applied to a hygienic material such as a paper diaper, a sanitary napkin, and an incontinence pad.

The invention claimed is:

1. A method of producing a polyacrylic acid (salt)-based water absorbent resin for use in an absorbent article, the method comprising:
    a polymerization step of polymerizing an aqueous monomer solution containing acrylic acid (salt) as a main component;
    a drying step of drying a water-containing gel-like crosslinked polymer obtained in the polymerization step;
    a surface crosslinking step of surface crosslinking the water absorbent resin under drying or the water absorbent resin which has been dried, in which a proportion of particles of the water absorbent resin that do not pass through a sieve having a mesh size of 850 µm is 0% to 5% by weight, relative to the total amount of the water absorbent resin;
    a packaging step of packaging the surface crosslinked water absorbent resin; and
    a storage step of storing the packaged water absorbent resin in a powder state for 3 days or longer until the packaged water absorbent resin is shipped to a user,
    wherein an iron content in the aqueous monomer solution in the polymerization step is 2 ppm or less, a moisture content of the water absorbent resin in the packaging step is 1% by weight or more, a packaging container used in the packaging step is a plastic container or a container having a plastic inner bag, the packaging container capable of transporting the water absorbent resin in a powder state, instead of transporting an absorbent article, in a unit amount of 15 kg to 10 t, and an amount of residual monomers of the water absorbent resin that has been subjected to the storage step is reduced by 0.5% to 30%, relative to an amount of residual monomers in the packaging step.

2. The method according to claim 1, wherein the packaged water absorbent resin is stored for 3 days to 100 days.

3. The method according to claim 1, wherein a content of p-methoxyphenol in the aqueous monomer solution in the polymerization step is 5 ppm to 160 ppm by weight, and a content of p-methoxyphenol in the water absorbent resin in the packaging step is 5 ppm to 60 ppm by weight.

4. The method according to claim 1, wherein a total content of acetic acid and propionic acid in the aqueous monomer solution in the polymerization step is 1500 ppm by weight or less.

5. The method according to claim 1, wherein the moisture content of the water absorbent resin in the packaging step is 3% to 20% by weight.

6. The method according to claim 1, further comprising, during or before the packaging step, a step of adding at least one or more aggregation preventing agents selected from the group consisting of polyvalent metal salts, water-insoluble fine particles, and surfactants to the water absorbent resin.

7. The method according to claim 1, further comprising, during or before the packaging step, a step of adding at least one or more coloration preventing agents selected from the group consisting of α-hydroxycarboxylic acid compounds, inorganic reducing agents, and chelating agents.

8. The method according to claim 1, wherein a travel distance for the water absorbent resin in the storage step is 10 km or less.

9. The method according to claim 1, wherein in the surface crosslinking step, surface crosslinking is carried out by using a crosslinking agent other than an epoxy-based crosslinking agent.

10. The method according to claim 1, wherein in the surface crosslinking step, surface crosslinking is carried out by using a dehydration reactive surface crosslinking agent.

11. The method according to claim 1, wherein the storage step is carried out in a storage place equipped with an apparatus for controlling at least one or more of air temperature and humidity.

12. The method according to claim 1, wherein a temperature and relative humidity in a place for storing the packaged water absorbent resin in the storage step is 0° C. to 35° C. and the 10% to 90%, respectively.

13. The method according to claim 1, wherein physical properties of the water absorbent resin are measured at least one or more times during the storage step.

14. The method according to claim 1, wherein the aqueous monomer solution in the polymerization step contains ammonium acrylate in an amount of equal to or more than 1% by mole and less than 90% by mole relative to the total amount of the monomer(s).

15. The method according to claim 1, wherein the water absorbent resin is stored in the storage step until an amount of residual monomers decreases by 10 ppm or more, and the amount of residual monomers in the water absorbent resin after the storage step is 500 ppm or less.

16. The method according to claim 1, further comprising a step of producing acrylic acid,
    wherein the acrylic acid production step is connected via pipelines with the process for producing the water absorbent resin in which the polymerization step through the packaging step are substantially connected;
    acrylic acid and/or vapor generated in the acrylic acid production step is supplied to the process for producing the water absorbent resin by using the pipelines; and
    the packaging step is contiguous with the storage step.

17. The method according to claim 16, wherein the acrylic acid production step is a distillation and/or crystallization step to produce acrylic acid, and the acrylic acid thus obtained is supplied to the polymerization step within 30 days after its production.

18. A method of producing a polyacrylic acid (salt)-based water absorbent resin for use in an absorbent article, the method comprising:
- a polymerization step of polymerizing an aqueous monomer solution containing acrylic acid (salt) as a main component;
- a drying step of drying a water-containing gel-like crosslinked polymer obtained in the polymerization step;
- a surface crosslinking step of surface crosslinking the water absorbent resin under drying or the water absorbent resin which has been dried, in which a proportion of particles of the water absorbent resin that do not pass through a sieve having a mesh size of 850 μm is 0% to 5% by weight, relative to the total amount of the water absorbent resin;
- a packaging step of packaging the surface crosslinked water absorbent resin; and
- a storage step of storing the packaged water absorbent resin in a powder state at a temperature of 0° C. to 60° C. and at a relative humidity of 10% to 90% for 3 days or longer until the packaged water absorbent resin is shipped to a user, wherein an iron content in the aqueous monomer solution in the polymerization step is 2 ppm or less, a moisture content of the water absorbent resin in the packaging step is 1% by weight or more, a packaging container used in the packaging step is a plastic container or a container having a plastic inner bag, the packaging container capable of transporting the water absorbent resin in a powder state, instead of transporting an absorbent article, in a unit amount of 15 kg to 10 t, and an amount of residual monomers of the water absorbent resin that has been subjected to the storage step is reduced by 0.5% to 30%, relative to an amount of residual monomers in the packaging step.

19. The method of claim 18, wherein the packaged water absorbent resin is stored at a temperature of 20° C. to 30° C. and at a relative humidity of 30% to 70%.

20. The method according to claim 1, wherein the moisture content of the water absorbent resin in the packaging step is 10% to 20% by weight.

* * * * *